(12) United States Patent
Bublot et al.

(10) Patent No.: US 6,497,883 B1
(45) Date of Patent: Dec. 24, 2002

(54) PORCINE CIRCOVIRUS RECOMBINANT POXVIRUS VACCINE

(75) Inventors: Michel Bublot, Delmar, NY (US); Jennifer M. Perez, East Nassau, NY (US); Catherine E. Charreyre, St.-Laurent De Mure (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/583,545

(22) Filed: Jun. 1, 2000

Related U.S. Application Data

(60) Provisional application No. 60/138,478, filed on Jun. 10, 1999.

(51) Int. Cl.[7] .......................... A61K 39/12; C12N 15/00
(52) U.S. Cl. ................. 424/204.1; 424/199.1; 424/209.1; 424/218.1; 435/320.1; 435/235.1; 536/23.72
(58) Field of Search ................ 424/199.1, 204.1, 424/209.1, 218.1; 536/23.72; 435/320.1, 235.1

(56) References Cited

U.S. PATENT DOCUMENTS

| | | | |
|---|---|---|---|
| 5,382,425 A | 1/1995 | Cochran et al. | |
| 5,587,164 A | * 12/1996 | Sanderson et al. | ........ 424/218.1 |
| 5,756,103 A | * 5/1998 | Paoletti et al. | ........... 424/199.1 |
| 5,770,212 A | 6/1998 | Falkner et al. | |
| 5,820,869 A | 10/1998 | Wasmoen et al. | |
| 5,833,975 A | 11/1998 | Paoletti et al. | |
| 5,990,091 A | 11/1999 | Tartaglia et al. | |
| 6,004,777 A | 12/1999 | Tartaglia et al. | |
| 6,033,904 A | 3/2000 | Cochran et al. | |
| 6,368,601 B1 | 4/2002 | Allan et al. | |

FOREIGN PATENT DOCUMENTS

| | | | |
|---|---|---|---|
| FR | 2769322 | * | 4/1999 |
| WO | WO 99/18214 | * | 4/1999 |

* cited by examiner

*Primary Examiner*—Ali R. Salimi
(74) *Attorney, Agent, or Firm*—Frommer Lawrence & Haug, LLP; William S. Frommer; Thomas J. Kowalski

(57) ABSTRACT

What is described is a recombinant poxvirus, such as avipox virus, containing foreign DNA from porcine circovirus 2. What are also described are immunological compositions containing the recombinant poxvirus for inducing an immunological response in a host animal to which the immunological composition is administered. Also described are methods of treating or preventing disease caused by porcine circovirus 2 by administering the immunological compositions of the invention to an animal in need of treatment or susceptible to infection by porcine circovirus 2.

26 Claims, 11 Drawing Sheets

FIG. 1A

HindIII (1)

```
   1 AAGCTTCTATCAAAAGTCTTAATGAGTTAGGTGTAGATAGTATAGATATTACTACAAAGGTATTCATATT

71 TCCTATCAATTCTAAAGTAGATGATATTAATAACTCAAAGATGATGATAGTAGATAATAGATACGCTCAT

141 ATAATGACTGCAAATTTGGACGGTTCACATTTTAATCATCACGCGTTCATAAGTTTCAACTGCATAGATC

211 AAAATCTCACTAAAAAGATAGCCGATGTATTTGAGAGAGATTGGACATCTAACTACGCTAAAGAAATTAC

281 AGTTATAAATAATACATAATGGATTTTGTTATCATCAGTTATATTTAACATAAGTACAATAAAAAGTATT

351 AAATAAAAATACTTACTTACGAAAAAATGTCATTATTACAAAAACTATATTTTACAGAACAATCTATAGT
                              1▶MetSerLeuLeuGlnLysLeuTyrPheThrGluGlnSerIleVa

421 AGAGTCCTTTAAGAGTTATAATTTAAAAGATAACCATAATGTAATATTTACCACATCAGATGATGATACT
  15▶lGluSerPheLysSerTyrAsnLeuLysAspAsnHisAsnValIlePheThrThrSerAspAspAspThr

491 GTTGTAGTAATAAATGAAGATAATGTACTGTTATCTACAAGATTATTATCATTTGATAAAATTCTGTTTT
  39▶ValValValIleAsnGluAspAsnValLeuLeuSerThrArgLeuLeuSerPheAspLysIleLeuPheP

561 TTAACTCCTTTAATAACGGTTTATCAAAATACGAAACTATTAGTGATACAATATTAGATATAGATACTCA
  62▶heAsnSerPheAsnAsnGlyLeuSerLysTyrGluThrIleSerAspThrIleLeuAspIleAspThrHi

631 TAATTATTATATACCTAGTTCTTCTTCTTTGTTAGATATTCTAAAAAAAAGAGCGTGTGATTTAGAATTA
  85▶sAsnTyrTyrIleProSerSerSerSerLeuLeuAspIleLeuLysLysArgAlaCysAspLeuGluLeu

701 GAAGATCTAAATTATGCGTTAATAGGAGACAATAGTAACTTATATTATAAAGATATGACTTACATGAATA
 109▶GluAspLeuAsnTyrAlaLeuIleGlyAspAsnSerAsnLeuTyrTyrLysAspMetThrTyrMetAsnA

771 ATTGGTTATTTACTAAAGGATTATTAGATTACAAGTTTGTATTATTGCGCGATGTAGATAAATGTTACAA
 132▶snTrpLeuPheThrLysGlyLeuLeuAspTyrLysPheValLeuLeuArgAspValAspLysCysTyrLy
```

Nrul (880)          Ndel (901)

```
 841 ACAGTATAATAAAAAGAATACTATAATAGATATAATACATCGCGATAACAGACAGTATAACATATGGGTT
 155▶sGlnTyrAsnLysLysAsnThrIleIleAspIleIleHisArgAspAsnArgGlnTyrAsnIleTrpVal

911 AAAAATGTTATAGAATACTGTTCTCCTGGCTATATATTATGGTTACATGATCTAAAAGCCGCTGCTGAAG
 179▶LysAsnValIleGluTyrCysSerProGlyTyrIleLeuTrpLeuHisAspLeuLysAlaAlaAlaGluA

981 ATGATTGGTTAAGATACGATAACCGTATAAACGAATTATCTGCGGATAAATTATACACTTTCGAGTTCAT
 202▶spAspTrpLeuArgTyrAspAsnArgIleAsnGluLeuSerAlaAspLysLeuTyrThrPheGluPheIl

1051 AGTTATATTAGAAAATAATATAAAACATTTACGAGTAGGTACAATAATTGTACATCCAAACAAGATAATA
 225▶eValIleLeuGluAsnAsnIleLysHisLeuArgValGlyThrIleIleValHisProAsnLysIleIle

1121 GCTAATGGTACATCTAATAATATACTTACTGATTTTCTATCTTACGTAGAAGAACTAATATATCATCATA
 249▶AlaAsnGlyThrSerAsnAsnIleLeuThrAspPheLeuSerTyrValGluGluLeuIleTyrHisHisA
```

EcoRI (1223)

```
1191 ATTCATCTATAATATTGGCCGGATATTTTTAGAATTCTTTGAGACCACTATTTTATCAGAATTTATTTC
 272▶snSerSerIleIleLeuAlaGlyTyrPheLeuGluPhePheGluThrThrIleLeuSerGluPheIleSe

1261 TTCATCTTCTGAATGGGTAATGAATAGTAACTGTTTAGTACACCTGAAAACAGGGTATGAAGCTATACTC
 295▶rSerSerSerGluTrpValMetAsnSerAsnCysLeuValHisLeuLysThrGlyTyrGluAlaIleLeu

1331 TTTGATGCTAGTTTATTTTTCCAACTCTCTACTAAAAGCAATTATGTAAAATATTGGACAAAGAAAACTT
 319▶PheAspAlaSerLeuPhePheGlnLeuSerThrLysSerAsnTyrValLysTyrTrpThrLysLysThrL

1401 TGCAGTATAAGAACTTTTTTAAAGACGGTAAACAGTTAGCAAAATATATAATTAAGAAAGATAGTCAGGT
 342▶euGlnTyrLysAsnPhePheLysAspGlyLysGlnLeuAlaLysTyrIleIleLysLysAspSerGlnVa
```

FIG. 1B

```
1471 GATAGATAGAGTATGTTATTTACAAGCAGCTGTATATAATCACGTAACTTACTTAATGGATACGTTTAAA
365▶ I I I eAspArgVa l CysTy rLeuHi sAl aAl aVa l TyrAsnHi sVa l Thr TyrLeuMetAspThr PheLys

1541 ATTCCTGGTTTTGATTTTAAATTCTCCGGAATGATAGATATACTACTGTTTGGAATATTGCATAAGGATA
389▶ I I eP roGl yPheAspPheLysPheSer Gl yMet I I I eAsp I I eLeuLeuPheGl y I I eLeuHi sLysAspA

1611 ATGAGAATATATTTTATCCGAAACGTGTTTCTGTAACTAATATAATATCAGAATCTATCTATGCAGATTT
412▶ snGl uAsn I I ePheT y rP roLysArgVa l Ser Va l ThrAsn I I e l I eSer Gl uSer I I eTyrAl aAspPh

1681 TTACTTTATATCAGATGTTAATAAATTCAGTAAAAAGATAGAATATAAAACTATGTTTCCTATACTCGCA
435▶ eTy rPhe I I eSerAspVa l AsnLysPheSer LysLys I I eGl uTyrLysThr Met PheP ro I I eLeuAl a

1751 GAAAACTACTATCCAAAAGGAAGGCCCTATTTTACACATACATCTAACGAAGATCTTCTGTCTATCTGTT
459▶ Gl uAsnTy rTy rP roLysGl yA rgP roTyrPheThr Hl sThr SerAsnGl uAspLeuLeuSer I I eCysL

1821 TATGCGAAGTAACAGTTTGTAAAGATATAAAAAATCCATTATTATATTCTAAAAAGGATATATCAGCAAA
482▶ euCysGl uVa l Thr Va l CysLysAsp I I eLysAsnP roLeuLeuT yrSer LysLysAsp I I eSer Al aLy

1891 ACGATTCATAGGTTTATTTACATCTGTCGATATAAATACGGCTGTTGAGTTAAGAGGATATAAAATAAGA
505▶ sArgPhe I I eGl yLeuPheThr Ser Va l Asp I I eAsnThr Al aVa l Gl uLeuArgGl yTyrLys I I eArg

1961 GTAATAGGATGTTTAGAATGGCCTGAAAAGATAAAAATATTTAATTCTAATCCTACATACATTAGATTAT
529▶ Va l I I eGl yCysLeuGl uT rpP roGl uLys I I eLys I I ePheAsnSerAsnP roThr Tyr I I eArgLeuL

2031 TACTAACAGAAAGACGTTTAGATATTCTACATTCCTATCTGCTTAAATTTAATATAACAGAGGATATAGC
552▶ euLeuThr Gl uArgArgLeuAsp I I eLeuHi sSer TyrLeuLeuLysPheAsn I I eThr Gl uAsp I I eAl

2101 TACCAGAGATGGAGTCAGAAATAATTTACCTATAATTTCTTTTATCGTCAGTTATTGTAGATCGTATACT
575▶ aThr A rgAspGl yVa l A rgAsnAsnLeuP ro I I e I I eSer Phe I I eVa l Ser TyrCysArgSer TyrThr

Ndel (2189)
2171 TATAAATTACTAAATTGCCATATGTACAATTCGTGTAAGATAACAAAGTGTAAATATAATCAGGTAATAT
599▶ TyrLysLeuLeuAsnCysHi sMet TyrAsnSer CysLys I I eThr LysCysLysTyrAsnGl nVa l I I eT 2241 ATAATCCTATATAGGAGTATATATAATTGAAAAAGTAAAATATAAATCATATAATAATGAAACGAAATAT
622▶ y rAsnP ro I I e• • •

2311 CAGTAATAGACAGGAACTGGCAGATTCTTCTTCTAATGAAGTAAGTACTGCTAAATCTCCAAAATTAGAT

2381 AAAAATGATACAGCAAATACAGCTTCATTCAACGAATTACCTTTTAATTTTTTCAGACACACCTTATTAC

2451 AAACTAACTAAGTCAGATGATGAGAAAGTAAATATAAATTTAACTTATGGGTATAATATAATAAAGATTC

2521 ATGATATTAATAATTTACTTAACGATGTTAATAGACTTATTCCATCAACCCCTTCAAACCTTTCTGGATA

2591 TTATAAAATACCAGTTAATGATATTAAAATAGATTGTTTAAGAGATGTAAATAATTATTTGGAGGTAAAG

2661 GATATAAAATTAGTCTATCTTTCACATGGAAATGAATTACCTAATATTAATAATTATGATAGGAATTTTT

2731 TAGGATTTACAGCTGTTATATGTATCAACAATACAGGCAGATCTATGGTTATGGTAAAACACTGTAACGG

2801 GAAGCAGCATTCTATGGTAACTGGCCTATGTTTAATAGCCAGATCATTTTACTCTATAAACATTTTACCA

BamHI (2880)
2871 CAAATAATAGGATCCTCTAGATATTTAATATTATATCTAACAACAACAAAAAAATTTAACGATGTATGGC

2941 CAGAAGTATTTTCTACTAATAAAGATAAAGATAGTCTATCTTATCTACAAGATATGAAAGAAGATAATCA

HindIII (3058)
3011 TTTAGTAGTAGCTACTAATATGGAAAGAAATGTATACAAAAACGTGGAAGCTTTTATATTAAATAGCATA

3081 TTACTAGAAGATTTAAAATCTAGACTTAGTATAACAAAACAGTTAAATGCCAATATCGATTCTATATTTC
```

FIG. 1C

```
3151  ATCATAACAGTAGTACATTAATCAGTGATATACTGAAACGATCTACAGACTCAACTATGCAAGGAATAAG
3221  CAATATGCCAATTATGTCTAATATTTTAACTTTAGAACTAAAACGTTCTACCAATACTAAAAATAGGATA
3291  CGTGATAGGCTGTTAAAAGCTGCAATAAATAGTAAGGATGTAGAAGAAATACTTTGTTCTATACCTTCGG
3361  AGGAAAGAACTTTAGAACAACTTAAGTTTAATCAAACTTGTATTTATGAACACTATAAAAAAATTATGGA
3431  AGATACAAGTAAAAGAATGGATGTTGAATGTCGTAGTTTAGAACATAACTATACGGCTAACTTATATAAA
3501  GTGTACGGACAAAACGAATATATGATTACTTATATACTAGCTCTCATAAGTAGGATTAATAATATTATAG
3571  AAACTTTAAAATATAATCTGGTGGGGCTAGACGAATCTACAATACGTAATATAAATTATATAATTTCACA
3641  AAGAACAAAAAAAAATCAAGTTTCTAATACCTTATAGATAAACTATATTTTTTACCACTGA
```

FIG. 3A

Kpnl (1)

1 GGTACCTTCATAAATACAAGTTTGATTAAACTTAAGTTGTTCTAAAGTTCTTTCCTCCGAAGGTATAGAA

71 CAAAGTATTTCTTCTACATCCTTACTATTTATTGCAGCTTTTAACAGCCTATCACGTATCCTATTTTTAG

141 TATTGGTAGAACGTTTTAGTTCTAAAGTTAAAATATTAGACATAATTGGCATATTGCTTATTCCTTGCAT

211 AGTTGAGTCTGTAGATCGTTTCAGTATATCACTGATTAATGTACTACTGTTATGATGAAATATAGAATCG

281 ATATTGGCATTTAACTGTTTTGTTATACTAAGTCTAGATTTTAAATCTTCTAGTAATATGCTATTTAATA

351 TAAAAGCTTCCACGTTTTTGTATACATTTCTTTCCATATTAGTAGCTACTACTAAATGATTATCTTCTTT

421 CATATCTTGTAGATAAGATAGACTATCTTTATCTTTATTAGTAGAAAATACTTCTGGCCATACATCGTTA

BamHI (532)
491 AATTTTTTTGTTGTTGTTAGATATAATATTAAATATCTAGAGGATCCTATTATTTGTGGTAAAATGTTTA

561 TAGAGTAAAATGATCTGGCTATTAAACATAGGCCAGTTACCATAGAATGCTGCTTCCCGTTACAGTGTTT

631 TACCATAACCATAGATCTGCCTGTATTGTTGATACATATAACAGCTGTAAATCCTAAAAAATTCCTATCA

701 TAATTATTAATATTAGGTAATTCATTTCCATGTGAAAGATAGACTAATTTTATATCCTTTACCTCCAAAT

771 AATTATTTACATCTCTTAAACAATCTATTTTAATATCATTAACTGGTATTTTATAATATCCAGAAAGGTT

841 TGAAGGGGTTGATGGAATAAGTCTATTAACATCGTTAAGTAAATTATTAATATCATGAATCTTTATTATA

911 TTATACCCATAAGTTAAATTTATATTTACTTTCTCATCATCTGACTTAGTTAGTTTGTAATAAGGTGTGT

981 CTGAAAAAATTAAAAGGTAATTCGTTGAATGAAGCTGTATTTGCTGTATCATTTTTATCTAATTTTGGAG

1051 ATTTAGCAGTACTTACTTCATTAGAAGAAGAATCTGCCAGTTCCTGTCTATTACTGATATTTCGTTTCAT

EcoRI (1
1121 TATTATATGATTTATATTTTACTTTTTCAATTATATATACTCATTTGACTAGTTAATCAATAAAAAGAAT

1191 TCCTGCAGCCCTGCAGCTAATTAATTAAGCTACAAATAGTTTCGTTTTCACCTTGTCTAATAACTAATTA

BamHI (1266)
1261 ATTAAGGATCCCCCAGCTTCTTTATTCTATACTTAAAAAGTGAAAATAAATACAAAGGTTCTTGAGGGTT

EcoRV (1378)
Nrul (1374)
1331 GTGTTAAATTGAAAGCGAGAAATAATCATAAATTATTTCATTATCGCGATATCCGTTAAGTTTGTATCGT 1401 AATGACGTATCCAAGGAGGCGTTACCGCAGAAGAAGACACCGCCCCCGCAGCCATCTTGGCCAGATCCTC
1▶ MetThr TyrProArgArgArgTyrArgArgArgArgHi sArgProArgSer HisLeuGlyGlnIleLeu 1471 CGCCGCCGCCCCTGGCTCGTCCACCCCGCCACCGCTACCGTTGGAGAAGGAAAAATGGCATCTTCAACA
24▶ ArgArgArgProTrpLeuValHisProArgHisArgTyrArgTrpArgArgLysAsnGlyIlePheAsnT 1541 CCCGCCTCTCCCGCACCTTCGGATATACTGTCAAGCGTACCACAGTCACAACGCCCTCCTGGGCGGTGGA
47▶ hr ArgLeuSer ArgThr PheGlyTyrThr ValLysArgThr Thr ValThr Thr ProSer TrpAlaValAs Smal (1644)
1611 CATGATGAGATTTAAAATTGACGACTTTGTTCCCCGGGAGGGGGGACCAACAAAATCTCTATACCCTTT
70▶ pMetMetArgPheLysIleAspAspPheValProProGlyGlyGlyThrAsnLysIleSerIleProPhe

FIG. 3B

```
         EcoRI (1711)
1681 GAATACTACAGAATAAGAAAGGTTAAGGTTGAATTCTGGCCCTGCTCCCCCATCACCCAGGGTGATAGGG
  94▶ GluTyrTyrArgIleArgLysValLysValGluPheTrpProCysSerProIleThrGlnGlyAspArgG

NdeI
1751 GAGTGGGCTCCACTGCTGTTATTCTAGATGATAACTTTGTAACAAAGGCCACAGCCCTAACCTATGACCC
 117▶ lyValGlySer Thr AlaValIleLeuAspAspAsnPheValThrLysAlaThrAlaLeuThr TyrAspPr

1821 ATATGTAAACTACTCCTCCCGCCATACAATCCCCCAACCCTTCTCCTACCACTCCCGTTACTTCACACCC
 140▶ oTyrValAsnTyrSerSerArgHisThrIleProGlnProPheSerTyrHisSerArgTyrPheThrPro

1891 AAACCTGTTCTTGACTCCACTATTGATTACTTCCAACCAAATAACAAAAGGAATCAGCTTTGGCTGAGAC
 164▶ LysProValLeuAspSerThrIleAspTyrPheGlnProAsnAsnLysArgAsnGlnLeuTrpLeuArgL

StuI (1989)
1961 TACAAACCTCTGGAAATGTGGACCACGTAGGCCTCGGCGCTGCGTTCGAAAACAGTAAATACGACCAGGA
 187▶ euGlnThr Ser GlyAsnValAspHisVal GlyLeuGlyAlaAlaPheGluAsnSer LysTyrAspGlnAs

2031 CTACAATATCCGTGTAACCATGTATGTACAATTCAGAGAATTTAATCTTAAAGACCCCCCACTTAAACCC
 210▶ pTyrAsnIleArgValThrMetTyrValGlnPheArgGluPheAsnLeuLysAspProProLeuLysPro

SmaI (2110)
         SalI (2104)
2101 TAAGTCGACCCCGGGTTTTTATAGCTAATTAGTCATTTTTTCGTAAGTAAGTATTTTTATTTAATACTTT

2171 TTATTGTACTTATGTTAAATATAACTGATGATAACAAAATCCATTATGTATTATTTATAACTGTAATTTC

2241 TTTAGCGTAGTTAGATGTCCAATCTCTCTCAAATACATCGGCTATCTTTTTAGTGAGATTTTGATCTATG

2311 CAGTTGAAACTTATGAACGCGTGATGATTAAAATGTGAACCGTCCAAATTTGCAGTCATTATATGAGCGT

2381 ATCTATTATCTACTATCATCATCTTTGAGTTATTAATATCATCTACTTTAGAATTGATAGGAAATATGAA

SacI (2515)
                                                             NotI (2507)
2451 TACCTTTGTAGTAATATCTATACTATCTACACCTAACTCATTAAGACTTTTGATAGGCGGCCGCGAGCTC
```

FIG. 6A

KpnI (1)

1 GGTACCTTCATAAATACAAGTTTGATTAAACTTAAGTTGTTCTAAAGTTCTTTCCTCCGAAGGTATAGAA

71 CAAAGTATTTCTTCTACATCCTTACTATTTATTGCAGCTTTTAACAGCCTATCACGTATCCTATTTTTAG

141 TATTGGTAGAACGTTTTAGTTCTAAAGTTAAAATATTAGACATAATTGGCATATTGCTTATTCCTTGCAT

211 AGTTGAGTCTGTAGATCGTTTCAGTATATCACTGATTAATGTACTACTGTTATGATGAAATATAGAATCG

281 ATATTGGCATTTAACTGTTTTGTTATACTAAGTCTAGATTTTAAATCTTCTAGTAATATGCTATTTAATA

351 TAAAAGCTTCCACGTTTTTGTATACATTTCTTTCCATATTAGTAGCTACTACTAAATGATTATCTTCTTT

421 CATATCTTGTAGATAAGATAGACTATCTTTATCTTTATTAGTAGAAAATACTTCTGGCCATACATCGTTA

BamHI (532)

491 AATTTTTTTGTTGTTGTTAGATATAATATTAAATATCTAGAGGATCCTATTATTTGTGGTAAAATGTTTA

561 TAGAGTAAAATGATCTGGCTATTAAACATAGGCCAGTTACCATAGAATGCTGCTTCCCGTTACAGTGTTT

631 TACCATAACCATAGATCTGCCTGTATTGTTGATACATATAACAGCTGTAAATCCTAAAAAATTCCTATCA

701 TAATTATTAATATTAGGTAATTCATTTCCATGTGAAAGATAGACTAATTTTATATCCTTTACCTCCAAAT

771 AATTATTTACATCTCTTAAACAATCTATTTTAATATCATTAACTGGTATTTTATAATATCCAGAAAGGTT

841 TGAAGGGGTTGATGGAATAAGTCTATTAACATCGTTAAGTAAATTATTAATATCATGAATCTTTATTATA

911 TTATACCCATAAGTTAAATTTATATTTACTTTCTCATCATCTGACTTAGTTAGTTTGTAATAAGGTGTGT

981 CTGAAAAAATTAAAAGGTAATTCGTTGAATGAAGCTGTATTTGCTGTATCATTTTTATCTAATTTTGGAG

1051 ATTTAGCAGTACTTACTTCATTAGAAGAAGAATCTGCCAGTTCCTGTCTATTACTGATATTTCGTTTCAT

1121 TATTATATGATTTATATTTTACTTTTTCAATTATATATACTCATTTGACTAGTTAATCAATAAAAAGAAT

1191 TTCGACTTAGGGTTTAAGTGGGGGGTCTTTAAGATTAAATTCTCTGAATTGTACATACATGGTTACACGG
         233◀ProLysLeuProProAspLysLeuAsnPheGluArgPheGlnValTyrMetThrValArgI

StuI (1306)

1261 ATATTGTAGTCCTGGTCGTATTTACTGTTTTCGAACGCAGCGCCGAGGCCTACGTGGTCCACATTTCCAG
    212◀leAsnTyrAspGlnAspTyrLysSerAsnGluPheAlaAlaGlyLeuGlyValHisAspValAsnGlySe

1331 AGGTTTGTAGTCTCAGCCAAAGCTGATTCCTTTTGTTATTTGGTTGGAAGTAATCAATAGTGGAGTCAAG
    189◀rThrGlnLeuArgLeuTrpLeuGlnAsnArgLysAsnAsnProGlnPheTyrAspIleThrSerAspLeu

1401 AACAGGTTTGGGTGTGAAGTAACGGGAGTGGTAGGAGAAGGGTTGGGGGATTGTATGGCGGGAGGAGTAG
    166◀ValProLysProThrPheTyrArgSerHisTyrSerPheProGlnProIleThrHisArgSerSerTyrA

NdeI (1475)

1471 TTTACATATGGGTCATAGGTTAGGGCTGTGGCCTTTGTTACAAAGTTATCATCTAGAATAACAGCAGTGG
    142◀snValTyrProAspTyrThrLeuAlaThrAlaLysThrValPheAsnAspAspLeuIleValAlaThrSe

EcoRI (1584)

1541 AGCCCACTCCCCTATCACCCTGGGTGATGGGGGAGCAGGGCCAGAATTCAACCTTAACCTTTCTTATTCT
    119◀rGlyValGlyArgAspGlyGlnThrIleProSerCysProTrpPheGluValLysValLysArgIleArg

SmaI (1651)

1611 GTAGTATTCAAAGGGTATAGAGATTTTGTTGGTCCCCCCTCCCGGGGGAACAAAGTCGTCAATTTTAAAT
    96◀TyrTyrGluPheProIleSerIleLysAsnThrGlyGlyGlyProProValPheAspAspIleLysPheA

FIG. 6B

```
1681 CTCATCATGTCCACCGCCCAGGAGGGCGTTGTGACTGTGGTACGCTTGACAGTATATCCGAAGGTGCGGG
  72◄rgMetMetAspValAlaTrpSerProThrThrValThrThrArgLysValThrTyrGlyPheThrArgSe

1751 AGAGGCGGGTGTTGAAGATGCCATTTTTCCTTCTCCAACGGTAGCGGTGGCGGGGGTGGACGAGCCAGGG
  49◄rLeuArgThrAsnPheIleGlyAsnLysArgArgTrpArgTyrArgHisArgProHisValLeuTrpPro

1821 GCGGCGGCGGAGGATCTGGCCAAGATGGCTGCGGGGCGGTGTCTTCTTCTGCGGTAACGCCTCCTTGGA
  26◄ArgArgArgLeuIleGlnGlyLeuHisSerArgProArgHisArgArgArgArgTyrArgArgArgProT
                              Nrul (1921)
                              EcoRV (1917)
1891 TACGTCATTACGATACAAACTTAACGGATATCGCGATAATGAAATAATTTATGATTATTTCTCGCTTTCA
   2◄yrThrMet

1961 ATTTAACACAACCCTCAAGAACCTTTGTATTTATTTTCACTTTTTAAGTATAGAATAAAGAAGCTGGGGG

2031 ATCAATTCCTGCAGCCCTGCAGCTAATTAATTAAGCTACAAATAGTTTCGTTTTCACCTTGTCTAATAAC
            BamHI (2112)
2101 TAATTAATTAAGGATCCCCCAGCTTCTTTATTCTATACTTAAAAAGTGAAAATAAATACAAAGGTTCTTG
                                                     EcoRV (2224)
                                                     Nrul (2220)
2171 AGGGTTGTGTTAAATTGAAAGCGAGAAATAATCATAAATTATTTCATTATCGCGATATCCGTTAAGTTTG 2241 TATCGTAATGCCCAGCAAGAAGAATGGAAGAAGCGGACCCCAACCACATAAAAGGTGGGTGTTCACGCTG
   1►MetProSerLysLysAsnGlyArgSerGlyProGlnProHisLysArgTrpValPheThrLeu
                    SacI (2347)
2311 AATAATCCTTCCGAAGACGAGCGCAAGAAAATACGGGAGCTCCCAATCTCCCTATTTGATTATTTTATTG
  22►AsnAsnProSerGluAspGluArgLysLysIleArgGluLeuProIleSerLeuPheAspTyrPheIleV 2381 TTGGCGAGGAGGGTAATGAGGAAGGACGAACACCTCACCTCCAGGGGTTCGCTAATTTTGTGAAGAAGCA
  45►alGlyGluGluGlyAsnGluGluGlyArgThrProHisLeuGlnGlyPheAlaAsnPheValLysLysGl
                                                                Bcll (2514)
2451 AACTTTTAATAAAGTGAAGTGGTATTTGGGTGCCCGCTGCCACATCGAGAAAGCCAAAGGAACTGATCAG
  68►nThrPheAsnLysValLysTrpTyrLeuGlyAlaArgCysHisIleGluLysAlaLysGlyThrAspGln
         SacI (2570)
2521 CAGAATAAAGAATATTGCAGTAAAGAAGGCAACTTACTTATTGAATGTGGAGCTCCTCGATCTCAAGGAC
  92►GlnAsnLysGluTyrCysSerLysGluGlyAsnLeuLeuIleGluCysGlyAlaProArgSerGlnGlyG 2591 AACGGAGTGACCTGTCTACTGCTGTGAGTACCTTGTTGGAGAGCGGGAGTCTGGTGACCGTTGCAGAGCA
 115►lnArgSerAspLeuSerThrAlaValSerThrLeuLeuGluSerGlySerLeuValThrValAlaGluGl 2661 GCACCCTGTAACGTTTGTCAGAAATTTCCGCGGGCTGGCTGAACTTTTGAAAGTGAGCGGGAAAATGCAG
 138►nHisProValThrPheValArgAsnPheArgGlyLeuAlaGluLeuLeuLysValSerGlyLysMetGln 2731 AAGCGTGATTGGAAGACCAATGTACACGTCATTGTGGGGCCACCTGGGTGTGGTAAAAGCAAATGGGCTG
 162►LysArgAspTrpLysThrAsnValHisValIleValGlyProProGlyCysGlyLysSerLysTrpAlaA
                                                              NcoI (2865
2801 CTAATTTTGCAGACCCGGAAACCACATACTGGAAACCACCTAGAAACAAGTGGTGGGATGGTTACCATGG
 185►laAsnPheAlaAspProGluThrThrTyrTrpLysProProArgAsnLysTrpAspGlyTyrHisGl 2871 TGAAGAAGTGGTTGTTATTGATGACTTTTATGGCTGGCTGCCGTGGGATGATCTACTGAGACTGTGTGAT
 208►yGluGluValValValIleAspAspPheTyrGlyTrpLeuProTrpAspAspLeuLeuArgLeuCysAsp
     EcoRV (2942)
2941 CGATATCCATTGACTGTAGAGACTAAAGGTGGAACTGTACCTTTTTTGGCCCGCAGTATTCTGATTACCA
 232►ArgTyrProLeuThrValGluThrLysGlyGlyThrValProPheLeuAlaArgSerIleLeuIleThrS
```

FIG. 6C

```
3011 GCAATCAGACCCCGTTGGAATGGTACTCCTCAACTGCTGTCCCAGCTGTAGAAGCTCTCTATCGGAGGAT
 255▶ er AsnGl nThr ProLeuGl uT rpTyrSer Ser Thr Al aVal ProAl aVal Gl uAl aLeuTyrArgArgI l

3081 TACTTCCTTGGTATTTTGGAAGAATGCTACAGAACAATCCACGGAGGAAGGGGGCCAGTTCGTCACCCTT
 278▶ eThr Ser LeuVal PheT rpLysAsnAl aThr Gl uGl nSer Thr Gl uGl uGl yGl yGl nPheVal Thr Leu

Smal (3199)
                            Ndel (3173)    Sall (3193)
3151 TCCCCCCCATGCCCTGAATTTCCATATGAAATAAATTACTGAGTCGACCCCGGGTTTTTATAGCTAATTA
 302▶ Ser ProProCysProGl uPheProTyrGl ul l eAsnTyr

3221 GTCATTTTTTCGTAAGTAAGTATTTTTATTTAATACTTTTTATTGTACTTATGTTAAATATAACTGATGA

3291 TAACAAAATCCATTATGTATTATTTATAACTGTAATTTCTTTAGCGTAGTTAGATGTCCAATCTCTCTCA

3361 AATACATCGGCTATCTTTTTAGTGAGATTTTGATCTATGCAGTTGAAACTTATGAACGCGTGATGATTAA

3431 AATGTGAACCGTCCAAATTTGCAGTCATTATATGAGCGTATCTATTATCTACTATCATCATCTTTGAGTT

3501 ATTAATATCATCTACTTTAGAATTGATAGGAAATATGAATACCTTTGTAGTAATATCTATACTATCTACA

Sacl (3604)
                         Notl (3596)
3571 CCTAACTCATTAAGACTTTTGATAGGCGGCCGCGAGCTC
```

SEQUENCE LISTING

<160> NUMBER OF SEQ ID NOS: 19

<210> SEQ ID NO 1
<211> LENGTH: 3701
<212> TYPE: DNA
<213> ORGANISM: Canarypox virus
<220> FEATURE:
<221> NAME/KEY: CDS
<222> LOCATION: (377)..(2251)

<400> SEQUENCE: 1

```
aagcttctat caaaagtctt aatgagttag gtgtagatag tatagatatt actacaaagg      60
tattcatatt tcctatcaat tctaaagtag atgatattaa taactcaaag atgatgatat     120
tagataatag atacgctcat ataatgactg caaatttgga cggttcacat tttaatcatc     180
acgcgttcat aagtttcaac tgcatagatc aaaatctcac taaaaagata gccgatgtat     240
ttgagagaga ttggacatct aactacgcta agaaattac agttataaat aatacataat      300
ggattttgtt atcatcagtt atatttaaca taagtacaat aaaaagtatt aaataaaaat     360
acttacttac gaaaaa atg tca tta tta caa aaa cta tat ttt aca gaa caa    412
                   Met Ser Leu Leu Gln Lys Leu Tyr Phe Thr Glu Gln
                     1               5                      10 tct ata gta gag tcc ttt aag agt tat aat tta aaa gat aac cat aat      460
Ser Ile Val Glu Ser Phe Lys Ser Tyr Asn Leu Lys Asp Asn His Asn
             15                  20                  25 gta ata ttt acc aca tca gat gat gat act gtt gta gta ata aat gaa      508
Val Ile Phe Thr Thr Ser Asp Asp Asp Thr Val Val Val Ile Asn Glu
         30                  35                  40 gat aat gta ctg tta tct aca aga tta tta tca ttt gat aaa att ctg      556
Asp Asn Val Leu Leu Ser Thr Arg Leu Leu Ser Phe Asp Lys Ile Leu
 45                  50                  55                  60 ttt ttt aac tcc ttt aat aac ggt tta tca aaa tac gaa act att agt      604
Phe Phe Asn Ser Phe Asn Asn Gly Leu Ser Lys Tyr Glu Thr Ile Ser
                 65                  70                  75 gat aca ata tta gat ata gat act cat aat tat tat ata cct agt tct      652
Asp Thr Ile Leu Asp Ile Asp Thr His Asn Tyr Tyr Ile Pro Ser Ser
             80                  85                  90 tct tct ttg tta gat att cta aaa aaa aga gcg tgt gat tta gaa tta      700
Ser Ser Leu Leu Asp Ile Leu Lys Lys Arg Ala Cys Asp Leu Glu Leu
         95                 100                 105 gaa gat cta aat tat gcg tta ata gga gac aat agt aac tta tat tat      748
Glu Asp Leu Asn Tyr Ala Leu Ile Gly Asp Asn Ser Asn Leu Tyr Tyr
    110                 115                 120 aaa gat atg act tac atg aat aat tgg tta ttt act aaa gga tta tta      796
Lys Asp Met Thr Tyr Met Asn Asn Trp Leu Phe Thr Lys Gly Leu Leu
125                 130                 135                 140 gat tac aag ttt gta tta ttg cgc gat gta gat aaa tgt tac aaa cag      844
Asp Tyr Lys Phe Val Leu Leu Arg Asp Val Asp Lys Cys Tyr Lys Gln
                145                 150                 155 tat aat aaa aag aat act ata ata gat ata ata cat cgc gat aac aga      892
Tyr Asn Lys Lys Asn Thr Ile Ile Asp Ile Ile His Arg Asp Asn Arg
            160                 165                 170
```

```
cag tat aac ata tgg gtt aaa aat gtt ata gaa tac tgt tct cct ggc      940
Gln Tyr Asn Ile Trp Val Lys Asn Val Ile Glu Tyr Cys Ser Pro Gly
        175                 180                 185 tat ata tta tgg tta cat gat cta aaa gcc gct gct gaa gat gat tgg      988
Tyr Ile Leu Trp Leu His Asp Leu Lys Ala Ala Ala Glu Asp Asp Trp
        190                 195                 200 tta aga tac gat aac cgt ata aac gaa tta tct gcg gat aaa tta tac     1036
Leu Arg Tyr Asp Asn Arg Ile Asn Glu Leu Ser Ala Asp Lys Leu Tyr
205                 210                 215                 220 act ttc gag ttc ata gtt ata tta gaa aat aat ata aaa cat tta cga     1084
Thr Phe Glu Phe Ile Val Ile Leu Glu Asn Asn Ile Lys His Leu Arg
                225                 230                 235 gta ggt aca ata att gta cat cca aac aag ata ata gct aat ggt aca     1132
Val Gly Thr Ile Ile Val His Pro Asn Lys Ile Ile Ala Asn Gly Thr
                240                 245                 250 tct aat aat ata ctt act gat ttt cta tct tac gta gaa gaa cta ata     1180
Ser Asn Asn Ile Leu Thr Asp Phe Leu Ser Tyr Val Glu Glu Leu Ile
                255                 260                 265 tat cat cat aat tca tct ata ata ttg gcc gga tat ttt tta gaa ttc     1228
Tyr His His Asn Ser Ser Ile Ile Leu Ala Gly Tyr Phe Leu Glu Phe
        270                 275                 280 ttt gag acc act att tta tca gaa ttt att tct tca tct tct gaa tgg     1276
Phe Glu Thr Thr Ile Leu Ser Glu Phe Ile Ser Ser Ser Ser Glu Trp
285                 290                 295                 300 gta atg aat agt aac tgt tta gta cac ctg aaa aca ggg tat gaa gct     1324
Val Met Asn Ser Asn Cys Leu Val His Leu Lys Thr Gly Tyr Glu Ala
                305                 310                 315 ata ctc ttt gat gct agt tta ttt ttc caa ctc tct act aaa agc aat     1372
Ile Leu Phe Asp Ala Ser Leu Phe Phe Gln Leu Ser Thr Lys Ser Asn
                320                 325                 330 tat gta aaa tat tgg aca aag aaa act ttg cag tat aag aac ttt ttt     1420
Tyr Val Lys Tyr Trp Thr Lys Lys Thr Leu Gln Tyr Lys Asn Phe Phe
                335                 340                 345 aaa gac ggt aaa cag tta gca aaa tat ata att aag aaa gat agt cag     1468
Lys Asp Gly Lys Gln Leu Ala Lys Tyr Ile Ile Lys Lys Asp Ser Gln
350                 355                 360 gtg ata gat aga gta tgt tat tta cac gca gct gta tat aat cac gta     1516
Val Ile Asp Arg Val Cys Tyr Leu His Ala Ala Val Tyr Asn His Val
365                 370                 375                 380 act tac tta atg gat acg ttt aaa att cct ggt ttt gat ttt aaa ttc     1564
Thr Tyr Leu Met Asp Thr Phe Lys Ile Pro Gly Phe Asp Phe Lys Phe
                385                 390                 395 tcc gga atg ata gat ata cta ctg ttt gga ata ttg cat aag gat aat     1612
Ser Gly Met Ile Asp Ile Leu Leu Phe Gly Ile Leu His Lys Asp Asn
                400                 405                 410 gag aat ata ttt tat ccg aaa cgt gtt tct gta act aat ata ata tca     1660
Glu Asn Ile Phe Tyr Pro Lys Arg Val Ser Val Thr Asn Ile Ile Ser
                415                 420                 425 gaa tct atc tat gca gat ttt tac ttt ata tca gat gtt aat aaa ttc     1708
Glu Ser Ile Tyr Ala Asp Phe Tyr Phe Ile Ser Asp Val Asn Lys Phe
        430                 435                 440 agt aaa aag ata gaa tat aaa act atg ttt cct ata ctc gca gaa aac     1756
Ser Lys Lys Ile Glu Tyr Lys Thr Met Phe Pro Ile Leu Ala Glu Asn
445                 450                 455                 460 tac tat cca aaa gga agg ccc tat ttt aca cat aca tct aac gaa gat     1804
Tyr Tyr Pro Lys Gly Arg Pro Tyr Phe Thr His Thr Ser Asn Glu Asp
                465                 470                 475 ctt ctg tct atc tgt tta tgc gaa gta aca gtt tgt aaa gat ata aaa     1852
Leu Leu Ser Ile Cys Leu Cys Glu Val Thr Val Cys Lys Asp Ile Lys
```

-continued

|  |  |  | 480 |  |  |  | 485 |  |  |  | 490 |  |  |  |
|---|---|---|---|---|---|---|---|---|---|---|---|---|---|---|
| aat | cca | tta | tta | tat | tct | aaa | aag | gat | ata | tca | gca | aaa | cga | ttc ata |
| Asn | Pro | Leu | Leu | Tyr | Ser | Lys | Lys | Asp | Ile | Ser | Ala | Lys | Arg | Phe Ile |
|  |  | 495 |  |  |  |  | 500 |  |  |  |  | 505 |  |  |

1900 ggt tta ttt aca tct gtc gat ata aat acg gct gtt gag tta aga gga    1948
Gly Leu Phe Thr Ser Val Asp Ile Asn Thr Ala Val Glu Leu Arg Gly
        510             515             520 tat aaa ata aga gta ata gga tgt tta gaa tgg cct gaa aag ata aaa    1996
Tyr Lys Ile Arg Val Ile Gly Cys Leu Glu Trp Pro Glu Lys Ile Lys
525             530             535             540 ata ttt aat tct aat cct aca tac att aga tta tta cta aca gaa aga    2044
Ile Phe Asn Ser Asn Pro Thr Tyr Ile Arg Leu Leu Leu Thr Glu Arg
            545             550             555 cgt tta gat att cta cat tcc tat ctg ctt aaa ttt aat ata aca gag    2092
Arg Leu Asp Ile Leu His Ser Tyr Leu Leu Lys Phe Asn Ile Thr Glu
        560             565             570 gat ata gct acc aga gat gga gtc aga aat aat tta cct ata att tct    2140
Asp Ile Ala Thr Arg Asp Gly Val Arg Asn Asn Leu Pro Ile Ile Ser
        575             580             585 ttt atc gtc agt tat tgt aga tcg tat act tat aaa tta cta aat tgc    2188
Phe Ile Val Ser Tyr Cys Arg Ser Tyr Thr Tyr Lys Leu Leu Asn Cys
        590             595             600 cat atg tac aat tcg tgt aag ata aca aag tgt aaa tat aat cag gta    2236
His Met Tyr Asn Ser Cys Lys Ile Thr Lys Cys Lys Tyr Asn Gln Val
605             610             615             620 ata tat aat cct ata taggagtata taattgaa aaagtaaaat ataaatcata      2291
Ile Tyr Asn Pro Ile
            625 taataatgaa acgaaatatc agtaatagac aggaactggc agattcttct tctaatgaag  2351 taagtactgc taaatctcca aaattagata aaaatgatac agcaaataca gcttcattca  2411 acgaattacc ttttaattttt ttcagacaca ccttattaca aactaactaa gtcagatgat  2471 gagaaagtaa atataaattt aacttatggg tataatataa taaagattca tgatattaat  2531 aatttactta acgatgttaa tagacttatt ccatcaaccc cttcaaacct ttctggatat  2591 tataaaatac cagttaatga tattaaaata gattgtttaa gagatgtaaa taattatttg  2651 gaggtaaagg atataaaatt agtctatctt tcacatggaa atgaattacc taatattaat  2711 aattatgata ggaattttttt aggatttaca gctgttatat gtatcaacaa tacaggcaga  2771 tctatggtta tggtaaaaca ctgtaacggg aagcagcatt ctatggtaac tggcctatgt  2831 ttaatagcca gatcatttta ctctataaac attttaccac aaataatagg atcctctaga  2891 tatttaatat tatatctaac aacaacaaaa aaatttaacg atgtatggcc agaagtatttt 2951 tctactaata agataaaga tagtctatct tatctacaag atatgaaaga agataatcat   3011 ttagtagtag ctactaatat ggaaagaaat gtatacaaaa acgtggaagc ttttttatatta 3071 aatagcatat tactagaaga tttaaaatct agacttagta taacaaaaca gttaaatgcc  3131 aatatcgatt ctatatttca tcataacagt agtacattaa tcagtgatat actgaaacga  3191 tctacagact caactatgca aggaataagc aatatgccaa ttatgtctaa tattttaact  3251 ttagaactaa aacgttctac caatactaaa aataggatac gtgataggct gttaaaagct  3311 gcaataaata gtaaggatgt agaagaaata ctttgttcta taccttcgga ggaaagaact  3371 ttagaacaac ttaagtttaa tcaaacttgt atttatgaac actataaaaa aattatggaa  3431 gatacaagta aaagaatgga tgttgaatgt cgtagtttag aacataacta tacggctaac  3491 ttatataaag tgtacggaca aaacgaatat atgattactt atatactagc tctcataagt  3551

```
aggattaata atattataga aactttaaaa tataatctgg tggggctaga cgaatctaca      3611
atacgtaata taaattatat aatttcacaa agaacaaaaa aaaatcaagt ttctaatacc      3671
ttatagataa actatatttt ttaccactga                                       3701
```

<210> SEQ ID NO 2
<211> LENGTH: 625
<212> TYPE: PRT
<213> ORGANISM: Canarypox virus

<400> SEQUENCE: 2

```
Met Ser Leu Leu Gln Lys Leu Tyr Phe Thr Glu Gln Ser Ile Val Glu
  1               5                  10                  15

Ser Phe Lys Ser Tyr Asn Leu Lys Asp Asn His Asn Val Ile Phe Thr
                 20                  25                  30

Thr Ser Asp Asp Asp Thr Val Val Ile Asn Glu Asp Asn Val Leu
             35                  40                  45

Leu Ser Thr Arg Leu Leu Ser Phe Asp Lys Ile Leu Phe Phe Asn Ser
 50                  55                  60

Phe Asn Asn Gly Leu Ser Lys Tyr Glu Thr Ile Ser Asp Thr Ile Leu
 65                  70                  75                  80

Asp Ile Asp Thr His Asn Tyr Tyr Ile Pro Ser Ser Ser Leu Leu
                 85                  90                  95

Asp Ile Leu Lys Lys Arg Ala Cys Asp Leu Glu Leu Glu Asp Leu Asn
                100                 105                 110

Tyr Ala Leu Ile Gly Asp Asn Ser Asn Leu Tyr Tyr Lys Asp Met Thr
            115                 120                 125

Tyr Met Asn Asn Trp Leu Phe Thr Lys Gly Leu Leu Asp Tyr Lys Phe
130                 135                 140

Val Leu Leu Arg Asp Val Asp Lys Cys Tyr Lys Gln Tyr Asn Lys Lys
145                 150                 155                 160

Asn Thr Ile Ile Asp Ile Ile His Arg Asp Asn Arg Gln Tyr Asn Ile
                165                 170                 175

Trp Val Lys Asn Val Ile Glu Tyr Cys Ser Pro Gly Tyr Ile Leu Trp
                180                 185                 190

Leu His Asp Leu Lys Ala Ala Glu Asp Asp Trp Leu Arg Tyr Asp
            195                 200                 205

Asn Arg Ile Asn Glu Leu Ser Ala Asp Lys Leu Tyr Thr Phe Glu Phe
210                 215                 220

Ile Val Ile Leu Glu Asn Asn Ile Lys His Leu Arg Val Gly Thr Ile
225                 230                 235                 240

Ile Val His Pro Asn Lys Ile Ile Ala Asn Gly Thr Ser Asn Asn Ile
                245                 250                 255

Leu Thr Asp Phe Leu Ser Tyr Val Glu Glu Leu Ile Tyr His His Asn
            260                 265                 270

Ser Ser Ile Ile Leu Ala Gly Tyr Phe Leu Glu Phe Glu Thr Thr
            275                 280                 285

Ile Leu Ser Glu Phe Ile Ser Ser Ser Glu Trp Val Met Asn Ser
        290                 295                 300

Asn Cys Leu Val His Leu Lys Thr Gly Tyr Glu Ala Ile Leu Phe Asp
305                 310                 315                 320

Ala Ser Leu Phe Phe Gln Leu Ser Thr Lys Ser Asn Tyr Val Lys Tyr
            325                 330                 335

Trp Thr Lys Lys Thr Leu Gln Tyr Lys Asn Phe Phe Lys Asp Gly Lys
```

```
                        340                 345                 350
        Gln Leu Ala Lys Tyr Ile Ile Lys Lys Asp Ser Gln Val Ile Asp Arg
                355                 360                 365
        Val Cys Tyr Leu His Ala Val Tyr Asn His Val Thr Tyr Leu Met
            370                 375                 380
        Asp Thr Phe Lys Ile Pro Gly Phe Asp Phe Lys Phe Ser Gly Met Ile
        385                 390                 395                 400
        Asp Ile Leu Leu Phe Gly Ile Leu His Lys Asp Asn Glu Asn Ile Phe
                        405                 410                 415
        Tyr Pro Lys Arg Val Ser Val Thr Asn Ile Ile Ser Glu Ser Ile Tyr
                    420                 425                 430
        Ala Asp Phe Tyr Phe Ile Ser Asp Val Asn Lys Phe Ser Lys Lys Ile
                435                 440                 445
        Glu Tyr Lys Thr Met Phe Pro Ile Leu Ala Glu Asn Tyr Tyr Pro Lys
            450                 455                 460
        Gly Arg Pro Tyr Phe Thr His Thr Ser Asn Glu Asp Leu Leu Ser Ile
        465                 470                 475                 480
        Cys Leu Cys Glu Val Thr Val Cys Lys Asp Ile Lys Asn Pro Leu Leu
                        485                 490                 495
        Tyr Ser Lys Lys Asp Ile Ser Ala Lys Arg Phe Ile Gly Leu Phe Thr
                    500                 505                 510
        Ser Val Asp Ile Asn Thr Ala Val Glu Leu Arg Gly Tyr Lys Ile Arg
                515                 520                 525
        Val Ile Gly Cys Leu Glu Trp Pro Glu Lys Ile Lys Ile Phe Asn Ser
            530                 535                 540
        Asn Pro Thr Tyr Ile Arg Leu Leu Leu Thr Glu Arg Arg Leu Asp Ile
        545                 550                 555                 560
        Leu His Ser Tyr Leu Leu Lys Phe Asn Ile Thr Glu Asp Ile Ala Thr
                        565                 570                 575
        Arg Asp Gly Val Arg Asn Asn Leu Pro Ile Ile Ser Phe Ile Val Ser
                    580                 585                 590
        Tyr Cys Arg Ser Tyr Thr Tyr Lys Leu Leu Asn Cys His Met Tyr Asn
                595                 600                 605
        Ser Cys Lys Ile Thr Lys Cys Lys Tyr Asn Gln Val Ile Tyr Asn Pro
            610                 615                 620
        Ile
        625

<210> SEQ ID NO 3
<211> LENGTH: 42
<212> TYPE: DNA
<213> ORGANISM: Canarypox virus

<400> SEQUENCE: 3
atcatcgagc tcgcggccgc ctatcaaaag tcttaatgag tt                          42

<210> SEQ ID NO 4
<211> LENGTH: 73
<212> TYPE: DNA
<213> ORGANISM: Canarypox virus

<400> SEQUENCE: 4
gaattcctcg agctgcagcc cgggttttta tagctaatta gtcatttttt cgtaagtaag      60
tatttttatt taa                                                         73
```

```
<210> SEQ ID NO 5
<211> LENGTH: 72
<212> TYPE: DNA
<213> ORGANISM: Canarypox virus

<400> SEQUENCE: 5
cccgggctgc agctcgagga attcttttta ttgattaact agtcaaatga gtatatataa      60
ttgaaaaagt aa                                                          72

<210> SEQ ID NO 6
<211> LENGTH: 45
<212> TYPE: DNA
<213> ORGANISM: Canarypox virus

<400> SEQUENCE: 6
gatgatggta ccttcataaa tacaagtttg attaaactta agttg                      45

<210> SEQ ID NO 7
<211> LENGTH: 53
<212> TYPE: DNA
<213> ORGANISM: Canarypox virus

<400> SEQUENCE: 7
catcatcatg atatccgtta agtttgtatc gtaatgacgt atccaaggag gcg             53

<210> SEQ ID NO 8
<211> LENGTH: 36
<212> TYPE: DNA
<213> ORGANISM: ALVAC

<400> SEQUENCE: 8
tactactacg tcgacttagg gtttaagtgg ggggtc                                36

<210> SEQ ID NO 9
<211> LENGTH: 2520
<212> TYPE: DNA
<213> ORGANISM: ALVAC
<220> FEATURE:
<221> NAME/KEY: CDS
<222> LOCATION: (1402)..(2100)

<400> SEQUENCE: 9
ggtaccttca taaatacaag tttgattaaa cttaagttgt tctaaagttc tttcctccga      60
aggtatagaa caaagtattt cttctacatc cttactattt attgcagctt ttaacagcct    120
atcacgtatc ctatttttag tattggtaga acgttttagt tctaaagtta aaatattaga    180
cataattggc atattgctta ttccttgcat agttgagtct gtagatcgtt tcagtatatc    240
actgattaat gtactactgt tatgatgaaa tatagaatcg atattggcat ttaactgttt    300
tgttatacta agtctagatt ttaaatcttc tagtaatatg ctatttaata taaaagcttc    360 cacgttttg tatacatttc tttccatatt agtagctact actaaatgat tatcttcttt     420
catatcttgt agataagata gactatcttt atctttatta gtagaaaata cttctggcca    480
tacatcgtta aattttttg ttgttgttag atataatatt aaatatctag aggatcctat     540
tatttgtggt aaaatgttta tagagtaaaa tgatctggct attaaacata ggccagttac    600
catagaatgc tgcttcccgt tacagtgttt taccataacc atagatctgc ctgtattgtt    660
gatacatata acagctgtaa atcctaaaaa attcctatca taattattaa tattaggtaa    720
ttcatttcca tgtgaaagat agactaattt tatatccttt acctccaaat aattatttac    780
atctcttaaa caatctattt taatatcatt aactggtatt ttataatatc cagaaaggtt    840
```

```
tgaaggggtt gatggaataa gtctattaac atcgttaagt aaattattaa tatcatgaat    900
ctttattata ttatacccat aagttaaatt tatatttact ttctcatcat ctgacttagt    960
tagtttgtaa taaggtgtgt ctgaaaaaat taaaaggtaa ttcgttgaat gaagctgtat   1020
ttgctgtatc attttatct aattttggag atttagcagt acttacttca ttagaagaag    1080
aatctgccag ttcctgtcta ttactgatat ttcgtttcat tattatatga tttatatttt   1140
acttttcaa ttatatatac tcatttgact agttaatcaa taaaaagaat tcctgcagcc    1200
ctgcagctaa ttaattaagc tacaaatagt ttcgttttca ccttgtctaa taactaatta   1260
attaaggatc ccccagcttc tttattctat acttaaaaag tgaaataaa tacaaaggtt    1320
cttgagggtt gtgttaaatt gaaagcgaga aataatcata aattatttca ttatcgcgat   1380
atccgttaag tttgtatcgt a atg acg tat cca agg agg cgt tac cgc aga     1431
                        Met Thr Tyr Pro Arg Arg Arg Tyr Arg Arg
                          1               5                  10 aga aga cac cgc ccc cgc agc cat ctt ggc cag atc ctc cgc cgc cgc    1479
Arg Arg His Arg Pro Arg Ser His Leu Gly Gln Ile Leu Arg Arg Arg
             15                  20                  25 ccc tgg ctc gtc cac ccc cgc cac cgc tac cgt tgg aga agg aaa aat   1527
Pro Trp Leu Val His Pro Arg His Arg Tyr Arg Trp Arg Arg Lys Asn
         30                  35                  40 ggc atc ttc aac acc cgc ctc tcc cgc acc ttc gga tat act gtc aag   1575
Gly Ile Phe Asn Thr Arg Leu Ser Arg Thr Phe Gly Tyr Thr Val Lys
             45                  50                  55 cgt acc aca gtc aca acg ccc tcc tgg gcg gtg gac atg atg aga ttt   1623
Arg Thr Thr Val Thr Thr Pro Ser Trp Ala Val Asp Met Met Arg Phe
         60                  65                  70 aaa att gac gac ttt gtt ccc ccg gga ggg ggg acc aac aaa atc tct   1671
Lys Ile Asp Asp Phe Val Pro Pro Gly Gly Gly Thr Asn Lys Ile Ser
75                  80                  85                  90 ata ccc ttt gaa tac tac aga ata aga aag gtt aag gtt gaa ttc tgg   1719
Ile Pro Phe Glu Tyr Tyr Arg Ile Arg Lys Val Lys Val Glu Phe Trp
                 95                 100                 105 ccc tgc tcc ccc atc acc cag ggt gat agg gga gtg ggc tcc act gct   1767
Pro Cys Ser Pro Ile Thr Gln Gly Asp Arg Gly Val Gly Ser Thr Ala
             110                 115                 120 gtt att cta gat gat aac ttt gta aca aag gcc aca gcc cta acc tat   1815
Val Ile Leu Asp Asp Asn Phe Val Thr Lys Ala Thr Ala Leu Thr Tyr
         125                 130                 135 gac cca tat gta aac tac tcc tcc cgc cat aca atc ccc caa ccc ttc   1863
Asp Pro Tyr Val Asn Tyr Ser Ser Arg His Thr Ile Pro Gln Pro Phe
     140                 145                 150 tcc tac cac tcc cgt tac ttc aca ccc aaa cct gtt ctt gac tcc act   1911
Ser Tyr His Ser Arg Tyr Phe Thr Pro Lys Pro Val Leu Asp Ser Thr
155                 160                 165                 170 att gat tac ttc caa cca aat aac aaa agg aat cag ctt tgg ctg aga   1959
Ile Asp Tyr Phe Gln Pro Asn Asn Lys Arg Asn Gln Leu Trp Leu Arg
                 175                 180                 185 cta caa acc tct gga aat gtg gac cac gta ggc ctc ggc gct gcg ttc   2007
Leu Gln Thr Ser Gly Asn Val Asp His Val Gly Leu Gly Ala Ala Phe
             190                 195                 200 gaa aac agt aaa tac gac cag gac tac aat atc cgt gta acc atg tat   2055
Glu Asn Ser Lys Tyr Asp Gln Asp Tyr Asn Ile Arg Val Thr Met Tyr
         205                 210                 215 gta caa ttc aga gaa ttt aat ctt aaa gac ccc cca ctt aaa ccc        2100
Val Gln Phe Arg Glu Phe Asn Leu Lys Asp Pro Pro Leu Lys Pro
     220                 225                 230
```

```
taagtcgacc ccgggttttt atagctaatt agtcattttt tcgtaagtaa gtatttttat    2160
ttaatacttt ttattgtact tatgttaaat ataactgatg ataacaaaat ccattatgta    2220
ttatttataa ctgtaatttc tttagcgtag ttagatgtcc aatctctctc aaatacatcg    2280
gctatctttt tagtgagatt ttgatctatg cagttgaaac ttatgaacgc gtgatgatta    2340
aaatgtgaac cgtccaaatt tgcagtcatt atatgagcgt atctattatc tactatcatc    2400
atctttgagt tattaatatc atctacttta gaattgatag gaaatatgaa tacctttgta    2460
gtaatatcta tactatctac acctaactca ttaagacttt tgataggcgg ccgcgagctc    2520
```

<210> SEQ ID NO 10
<211> LENGTH: 233
<212> TYPE: PRT
<213> ORGANISM: ALVAC

<400> SEQUENCE: 10

```
Met Thr Tyr Pro Arg Arg Arg Tyr Arg Arg Arg His Arg Pro Arg
 1               5                  10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Arg Thr Thr Val Thr Thr
        50                  55                  60

Pro Ser Trp Ala Val Asp Met Met Arg Phe Lys Ile Asp Asp Phe Val
    65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Gly Asn
            180                 185                 190

Val Asp His Val Gly Leu Gly Ala Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 11
<211> LENGTH: 57
<212> TYPE: DNA
<213> ORGANISM: ALVAC

<400> SEQUENCE: 11

```
catcatcatt cgcgatatcc gttaagtttg tatcgtaatg cccagcaaga agaatgg       57
```

<210> SEQ ID NO 12

-continued

```
<211> LENGTH: 36
<212> TYPE: DNA
<213> ORGANISM: ALVAC

<400> SEQUENCE: 12
tactactacg tcgactcagt aatttatttc atatgg                               36

<210> SEQ ID NO 13
<211> LENGTH: 3609
<212> TYPE: DNA
<213> ORGANISM: ALVAC

<400> SEQUENCE: 13
ggtaccttca taaatacaag tttgattaaa cttaagttgt tctaaagttc tttcctccga     60
aggtatagaa caaagtattt cttctacatc cttactattt attgcagctt ttaacagcct    120
atcacgtatc ctattttag tattggtaga acgttttagt tctaaagtta aaatattaga     180
cataattggc atattgctta ttccttgcat agttgagtct gtagatcgtt tcagtatatc    240
actgattaat gtactactgt tatgatgaaa tatagaatcg atattggcat ttaactgttt    300
tgttatacta agtctagatt ttaaatcttc tagtaatatg ctatttaata taaaagcttc    360 cacgttttg tatacatttc tttccatatt agtagctact actaaatgat tatcttcttt     420
catatcttgt agataagata gactatcttt atctttatta gtagaaaata cttctggcca    480
tacatcgtta aatttttttg ttgttgttag atataatatt aaatatctag aggatcctat    540
tatttgtggt aaaatgttta tagagtaaaa tgatctggct attaaacata ggccagttac    600
catagaatgc tgcttcccgt tacagtgttt taccataacc atagatctgc ctgtattgtt    660
gatacatata acagctgtaa atcctaaaaa attcctatca taattattaa tattaggtaa    720
ttcatttcca tgtgaaagat agactaattt tatatccttt acctccaaat aattatttac    780
atctcttaaa caatctatt taatatcatt aactggtatt ttataatatc cagaaaggtt     840 tgaagggtt gatggaataa gtctattaac atcgttaagt aaattattaa tatcatgaat     900
ctttattata ttataccccat aagttaaatt tatatttact ttctcatcat ctgacttagt    960
tagtttgtaa taggtgtgt ctgaaaaaat taaaaggtaa ttcgttgaat gaagctgtat    1020
ttgctgtatc attttatct aattttggag atttagcagt acttacttca ttagaagaag    1080
aatctgccag ttcctgtcta ttactgatat ttcgtttcat tattatatga tttatatttt    1140 acttttcaa ttatatatac tcatttgact agttaatcaa taaaaagaat ttcgacttag    1200
ggtttaagtg gggggtcttt aagattaaat tctctgaatt gtacatacat ggttacacgg    1260
atattgtagt cctggtcgta tttactgttt tcgaacgcag cgccgaggcc tacgtggtcc    1320
acatttccag aggtttgtag tctcagccaa agctgattcc ttttgttatt tggttggaag    1380
taatcaatag tggagtcaag aacaggtttg ggtgtgaagt aacgggagtg gtaggagaag    1440
ggttggggga ttgtatggcg ggaggagtag tttacatatg ggtcataggt tagggctgtg    1500
gcctttgtta caagttatc atctagaata acagcagtgg agcccactcc cctatcaccc    1560
tgggtgatgg gggagcaggg ccagaattca accttaacct ttcttattct gtagtattca    1620
aagggtatag agattttgtt ggtcccccct cccgggggaa caaagtcgtc aattttaaat    1680
ctcatcatgt ccaccgccca ggaggcgtt gtgactgtgg tacgcttgac agtatatccg     1740 aagtgcggg agaggcgggt gttgaagatg ccatttttcc ttctccaacg gtagcggtgg    1800 cggggtgga cgagccaggg gcggcggcgg aggatctggc caagatggct gcgggggcgg    1860
tgtcttcttc tgcggtaacg cctccttgga tacgtcatta cgatacaaac ttaacggata    1920
```

```
tcgcgataat gaaataattt atgattattt ctcgctttca atttaacaca accctcaaga    1980
acctttgtat ttattttcac tttttaagta tagaataaag aagctggggg atcaattcct    2040
gcagccctgc agctaattaa ttaagctaca aatagtttcg ttttcacctt gtctaataac    2100
taattaatta aggatccccc agcttcttta ttctatactt aaaaagtgaa aataaataca    2160
aaggttcttg agggttgtgt taaattgaaa gcgagaaata atcataaatt atttcattat    2220
cgcgatatcc gttaagtttg tatcgtaatg cccagcaaga agaatggaag aagcggaccc    2280
caaccacata aaaggtgggt gttcacgctg aataatcctt ccgaagacga gcgcaagaaa    2340
atacgggagc tcccaatctc cctatttgat tattttattg ttggcgagga gggtaatgag    2400
gaaggacgaa caccctcacct ccaggggttc gctaattttg tgaagaagca aacttttaat    2460
aaagtgaagt ggtatttggg tgcccgctgc cacatcgaga aagccaaagg aactgatcag    2520
cagaataaag aatattgcag taagaaggc aacttactta ttgaatgtgg agctcctcga    2580
tctcaaggac aacggagtga cctgtctact gctgtgagta ccttgttgga gagcgggagt    2640
ctggtgaccg ttgcagagca gcaccctgta acgtttgtca gaaatttccg cgggctggct    2700
gaacttttga aagtgagcgg gaaaatgcag aagcgtgatt ggaagaccaa tgtacacgtc    2760
attgtggggc cacctgggtg tggtaaaagc aaatgggctg ctaattttgc agacccggaa    2820
accacatact ggaaaccacc tagaaacaag tggtgggatg gttaccatgg tgaagaagtg    2880
gttgttattg atgactttta tggctggctg ccgtgggatg atctactgag actgtgtgat    2940
cgatatccat tgactgtaga gactaaaggt ggaactgtac cttttttggc ccgcagtatt    3000
ctgattacca gcaatcagac cccgttggaa tggtactcct caactgctgt cccagctgta    3060
gaagctctct atcggaggat tacttccttg gtattttgga agaatgctac agaacaatcc    3120
acggaggaag ggggccagtt cgtcacccctt tcccccccat gccctgaatt tccatatgaa    3180
ataaattact gagtcgaccc cgggtttta tagctaatta gtcattttt cgtaagtaag    3240 tatttttatt taatacttt tattgtactt atgttaaata taactgatga taacaaaatc    3300
cattatgtat tatttataac tgtaatttct ttagcgtagt tagatgtcca atctctctca    3360
aatacatcgg ctatctttt agtgagattt tgatctatgc agttgaaact tatgaacgcg    3420
tgatgattaa aatgtgaacc gtccaaattt gcagtcatta tatgagcgta tctattatct    3480
actatcatca tctttgagtt attaaatatca tctactttag aattgatagg aaatatgaat    3540 accttttgtag taatatctat actatctaca cctaactcat taagactttt gataggcggc    3600
cgcgagctc                                                            3609
```

<210> SEQ ID NO 14
<211> LENGTH: 236
<212> TYPE: PRT
<213> ORGANISM: ALVAC

<400> SEQUENCE: 14

Pro Lys Leu Pro Pro Asp Lys Leu Asn Phe Glu Arg Phe Gln Val Tyr
 1               5                  10                  15

Met Thr Val Arg Ile Asn Tyr Asp Gln Asp Tyr Lys Ser Asn Glu Phe
            20                  25                  30

Ala Ala Tyr Leu Tyr Val His Asp Val His Asp Val Asn Tyr Ser Thr
        35                  40                  45

Gln Leu Arg Leu Trp Leu Gln Asn Arg Lys Asn Asn Pro Gln Phe Tyr
    50                  55                  60

```
Asp Ile Thr Ser Asp Leu Val Pro Lys Pro Thr Phe Tyr Arg Ser His
 65                  70                  75                  80

Tyr Ser Phe Pro Gln Pro Ile Thr His Arg Ser Ser Tyr Gln Val Tyr
                 85                  90                  95

Pro Asp Tyr Thr Leu Ala Thr Ala Lys Thr Val Phe Gln Asp Asp Leu
            100                 105                 110

Ile Val Ala Thr Ser Gly Val Gly Arg Asp Gly Gln Thr Ile Pro Ser
        115                 120                 125

Cys Pro Trp Phe Glu Val Lys Val Lys Arg Ile Arg Tyr Tyr Glu Phe
    130                 135                 140

Pro Ile Ser Ile Lys Gln Thr Gly Gly Pro Pro Val Phe Asp Asp
145                 150                 155                 160

Ile Lys Phe Arg Met Met Asp Val Ala Trp Ser Pro Thr Thr Val Thr
                165                 170                 175

Thr Arg Lys Val Thr Tyr Gly Phe Thr Arg Ser Leu Arg Thr Asn Phe
            180                 185                 190

Ile Gly Asn Lys Arg Arg Trp Arg Tyr Arg His Arg Pro His Val Leu
        195                 200                 205

Trp Pro Arg Arg Arg Leu Ile Gln Gly Leu His Ser Arg Pro Arg His
    210                 215                 220

Arg Arg Arg Arg Tyr Arg Arg Pro Tyr Thr Met
225                 230                 235

<210> SEQ ID NO 15
<211> LENGTH: 314
<212> TYPE: PRT
<213> ORGANISM: ALVAC

<400> SEQUENCE: 15

Met Pro Ser Lys Lys Gln Gly Arg Ser Gly Pro Gln Pro His Lys Arg
  1               5                  10                  15

Trp Val Phe Thr Leu Asn Asn Pro Ser Glu Asp Glu Arg Lys Lys Ile
                 20                  25                  30

Arg Glu Leu Pro Ile Ser Leu Phe Asp Tyr Phe Ile Val Gly Glu Glu
             35                  40                  45

Gly Asn Glu Glu Gly Arg Thr Pro His Leu Gln Gly Phe Ala Asn Phe
         50                  55                  60

Val Lys Lys Gln Thr Phe Asn Lys Val Lys Arg Tyr Leu Gly Ala Arg
 65                  70                  75                  80

Cys His Ile Glu Lys Ala Lys Gly Thr Asp Gln Gln Asn Lys Glu Tyr
                 85                  90                  95

Cys Ser Lys Glu Gly Asn Leu Leu Ile Glu Cys Gly Ala Pro Arg Ser
            100                 105                 110

Gln Gly Gln Arg Ser Asp Leu Ser Thr Ala Val Ser Thr Leu Leu Glu
        115                 120                 125

Ser Gly Ser Leu Val Thr Val Ala Glu Gln His Pro Val Thr Phe Val
    130                 135                 140

Arg Asn Phe Arg Gly Leu Ala Glu Leu Leu Lys Val Ser Gly Lys Met
145                 150                 155                 160

Gln Lys Arg Asp Trp Lys Thr Asn Val His Val Ile Val Gly Pro Pro
                165                 170                 175

Gly Cys Gly Lys Ser Lys Trp Ala Ala Asn Phe Ala Asp Pro Glu Thr
            180                 185                 190

Thr Tyr Trp Lys Pro Pro Arg Asn Lys Trp Trp Asp Gly Tyr His Gly
        195                 200                 205
```

```
Glu Glu Val Val Val Ile Asp Asp Phe Tyr Gly Trp Leu Pro Trp Asn
    210                 215                 220

Asp Leu Leu Arg Leu Cys Asp Arg Tyr Pro Leu Thr Val Glu Thr Lys
225                 230                 235                 240

Gly Gly Thr Val Pro Phe Leu Ala Arg Ser Ile Leu Ile Thr Ser Asn
                245                 250                 255

Gln Thr Pro Leu Glu Trp Tyr Ser Ser Thr Ala Val Pro Ala Val Glu
            260                 265                 270

Ala Leu Tyr Arg Arg Ile Thr Ser Leu Val Phe Trp Lys Asn Ala Thr
        275                 280                 285

Glu Gln Ser Thr Glu Glu Gly Gly Gln Phe Val Thr Leu Ser Pro Pro
    290                 295                 300

Cys Pro Glu Phe Pro Tyr Glu Ile Asn Tyr
305                 310

<210> SEQ ID NO 16
<211> LENGTH: 53
<212> TYPE: DNA
<213> ORGANISM: ALVAC

<400> SEQUENCE: 16
catcatcatg atatccgtta agtttgtatc gtaatgacgt ggccaaggag gcg         53

<210> SEQ ID NO 17
<211> LENGTH: 40
<212> TYPE: DNA
<213> ORGANISM: ALVAC

<400> SEQUENCE: 17
tactactacg tcgacttatt tatttagagg gtcttttagg                        40

<210> SEQ ID NO 18
<211> LENGTH: 57
<212> TYPE: DNA
<213> ORGANISM: ALVAC

<400> SEQUENCE: 18
catcatcatt cgcgatatcc gttaagtttg tatcgtaatg ccaagcaaga aaagcgg     57

<210> SEQ ID NO 19
<211> LENGTH: 36
<212> TYPE: DNA
<213> ORGANISM: ALVAC

<400> SEQUENCE: 19
tactactacg tcgactcagt aatttatttt atatgg                           36
```

US 6,497,883 B1

PORCINE CIRCOVIRUS RECOMBINANT POXVIRUS VACCINE

CROSS REFERENCE TO RELATED APPLICATIONS

This application claims priority from U.S. application Ser. No. 60/138,478, filed Jun. 10, 1999. Reference is made to WO-A-99 18214, 1998, French applications Nos. 97/12382, 98/00873, 98/03707, filed Oct. 3, 1997, Jan. 22, 1998, and Mar. 20, 1998, and WO99/29717. Each of the aforementioned U.S., PCT and French applications, and each document cited in the text and the record or prosecution of each of the aforementioned U.S., PCT and French applications ("application cited documents") and each document referenced or cited in each of the application cited documents, is hereby incorporated herein by reference; and, technology in each of the aforementioned U.S., PCT and French applications, and each document cited in the text and the record or prosecution of each of the aforementioned U.S., PCT and French applications can be used in the practice of this invention.

Several publications are referenced in this application. Full citation to these documents is found at the end of the specification preceding the claims, and/or where the document is cited. These documents pertain to the field of this invention; and, each of the documents cited or referenced in this application ("herein cited documents") and each document cited or referenced in herein cited documents are hereby incorporated herein by reference.

FIELD OF THE INVENTION

The present invention relates to vectors, such as recombinant vectors; for instance, recombinant viruses, such as poxviruses, e.g., modified poxviruses and to methods of making and using the same. In some embodiments, the invention relates to recombinant avipox viruses, such as canarypox viruses, e.g., ALVAC. The invention further relates to such vectors, e.g., poxviruses, that express gene products, e.g., antigen(s), ORF(s), and/or epitope(s) of interest therefrom, of porcine circovirus 2 (PCV2); to immunological compositions or vaccines. The invention yet further relates to such vectors, e.g., poxviruses, that induce an immune response directed to or against PCV2 gene products and/or PCV2; and, to advantageously, such compositions that are immunological, immunogenic or vaccine compositions and/or confer protective immunity against infection by PCV2. The invention yet further relates to the uses of and methods for making and using such vectors and compositions, as well as intermediates thereof, and said intermediates. And, the invention relates to the products therefrom, e.g., from the uses and methods involving the inventive recombinant or poxvirus, such as antibodies from expression.

BACKGROUND OF THE INVENTION

Postweaning multisystemic wasting syndrome (PMWS) is a recently recognized disease of young pigs. PMWS is characterized clinically by progressive weight loss and other symptoms such as tachypnea, dyspnea and jaundice. Pathologically, lymphocytic and granulomatous infiltrates, lymphadenopathy, and, more rarely, lymphocytic and granulomatous hepatitis and nephritis have been observed (Clark, 1997; Harding, 1997).

This disease has been described in different European countries as well as in North America. Treatment and prevention of this disease are not currently available.

Several lines of evidence point to porcine circovirus as the etiologic agent of PMWS (Ellis et al., 1998). Circoviruses have been recovered from pigs with PMWS, and antibodies to porcine circovirus have been demonstrated in pigs with the disease.

Circoviruses are single stranded circular DNA viruses found in a range of animal and plant species. Porcine circovirus was originally isolated as a contaminant from a continuous pig kidney cell line. The cell culture isolate has been designated PK-15 (Meehan et al., 1997). More recently, porcine circovirus obtained from pigs with PMWS has been compared to PK-15. Such viruses differ substantially from PK-15 at the nucleotide and protein sequence level, and have been designated PCV2 (Meehan et al., 1998; Hamel et al., 1998).

As many as thirteen open reading frames (ORFs) have been identified in the PCV2 genome (COL1 to COL13 in the French patent application 98 03707). Four of these ORFs share substantial homology with analogous ORFs within the genome of PK-15. ORF1 (Meehan et al., 1998; corresponding to COL4 in the French patent application 98 03707), comprising nt 398-1342 (GenBank accession number AF055392), has the potential to encode a protein with a predicted molecular weight of 37.7 kD. ORF2 (Meehan et al., 1998; corresponding to COL13 in the French patent application 98 03707), comprising nt 1381-1768 joined to 1-314 (GenBank accession number AF055392), may encode a protein with a predicted molecular weight of 27.8 kD. ORF3 (Meehan et al., 1998; corresponding to COL7 in the French patent application 98 03707), comprising nt 1018-704 (GenBank accession number AF055392), may encode a protein with a predicted molecular weight of 11.9 kD. ORF4 (Meehan et al., 1998; corresponding to COL10 in the French patent application 98 03707), comprising nt 912-733 (GenBank accession number AF055392), may encode a protein with a predicted molecular weight of 6.5 kD.

ORF1 of PCV2 is highly homologous (86% identity) to the ORF1 of the PK-15 isolate (Meehan et al., 1998). The ORF1 protein of PK-15 has been partially characterized (Meehan et al., 1997; Mankertz et al., 1998a). It is known to be essential for virus replication, and is probably involved in the viral DNA replication.

Protein sequence identity between the respective ORF2s was lower (66% identity) than that of the ORF1s but each of the ORF2s shared a highly conserved basic N-terminal region, similar to that observed in the N-terminal region of the major structural protein of the avian circovirus chicken anemia virus (CAV) (Meehan et al., 1998). Recently, Mankertz et al. (1998b) has suggested that the ORF2 of the PK-15 isolate (designated ORF 1 in Mankertz et al., 1998b) codes for a capsid protein.

Greater differences were observed between the respective ORF3s and ORF4s of the PK-15 isolate and PCV2. In each case, there was a deletion of the C-terminal region of PCV2 ORF4 and ORF3 compared to the corresponding ORFs present in the genome of the PK-15 isolate. The highest protein sequence homology was observed at the N-terminal regions of both ORF3 and ORF4 (Meehan et al., 1998).

The transcription analysis of the genome of PCV2 has not been published yet. Recent data obtained with the PK-15 isolate indicated that the ORF2 transcript is spliced (Mankertz et al., 1998b).

Vaccinia virus has been used successfully to immunize against smallpox, culminating in the worldwide eradication of smallpox in 1980. With the eradication of smallpox, a new role for poxviruses became important, that of a genetically engineered vector for the expression of foreign genes (Panicali and Paoletti, 1982; Paoletti et al., 1984). Genes encoding heterologous antigens have been expressed in vaccinia, often resulting in protective immunity against challenge by the corresponding pathogen (reviewed in Tartaglia et al., 1990). A highly attenuated strain of vaccines, designated MVA, has also been used as a vector for poxvirus-based vaccines. Use of MVA is described in U.S. Pat. No. 5,185,146.

Two additional vaccine vector systems involve the use of naturally host-restricted poxviruses, avipox viruses. Both fowlpoxvirus (FPV; Taylor et al. 1988a, b) and canarypoxvirus (CPV; Taylor et al., 1991 & 1992) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988c). After inoculation of the recombinant into chickens and turkeys, an immune response was induced which was protective against either a homologous or a heterologous virulent influenza virus challenge (Taylor et al., 1988c). FPV recombinants expressing the surface glycoproteins of Newcastle Disease Virus have also been developed (Taylor et al., 1990; Edbauer et al., 1990).

Other attenuated poxvirus vectors have been prepared by genetic modifications of wild type strains of virus. The NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen.

Another engineered poxvirus vector is ALVAC, derived from canarypox virus (ALVAC was deposited with American Type Culture Collection, P.O. Box 1549, Manassas, Va. 20108, USA, under the terms of the Budapest Treaty on Nov. 14, 1996, and is designated as Accession Number VR-2547). ALVAC does not productively replicate in non-avian hosts, a characteristic thought to improve its safety profile (Taylor et al., 1991 & 1992). Both ALVAC and NYVAC are BSL-1 vectors.

One approach to the development of a subunit PCV2 vaccine is the use of live viral vectors to express relevant PCV2 ORFs. Recombinant poxviruses can be constructed in two steps known in the art and analogous to the methods for creating synthetic recombinants of poxviruses such as the vaccinia virus and avipox virus described in U.S. Pat. Nos. 4,769,330; 4,722,848; 4,603,112; 5,110,587; 5,174,993; 5,494,807; and 5,505,941, the disclosures of which are incorporated herein by reference. It can thus be appreciated that provision of a PCV2 recombinant poxvirus, and of compositions and products therefrom particularly ALVAC based PCV2 recombinants and compositions and products therefrom, especially such recombinants containing ORFs 1 and/or 2 of PCV2, and compositions and products therefrom would be a highly desirable advance over the current state of technology.

OBJECTS AND SUMMARY OF THE INVENTION

It is therefore an object of this invention to provide compositions and methods for treatment and prophylaxis of infection with PCV2. It is also an object to provide a means to treat or prevent PMWS.

In one aspect, the present invention relates to an antigenic, immunological, immunogenic, or vaccine composition or a therapeutic composition for inducing an antigenic, immunogenic or immunological response in a host animal inoculated with the composition. The composition advantageously includes a carrier or diluent and a recombinant virus, such as a recombinant poxvirus. The recombinant virus or poxvirus contains and expresses an exogenous nucleic acid molecule encoding an ORF, antigen, immunogen, or epitope of interest from PCV2, or a protein that elicits an immunological response against PCV2 or conditions caused by PCV2, such as PMWS. For instance, the recombinant virus can be a modified recombinant virus or poxvirus; for example, such a virus or poxvirus that has inactivated therein virus-encoded genetic functions, e.g., nonessential virus-encoded genetic functions, so that the recombinant virus has attenuated virulence and enhanced safety. And, the invention further provides the viruses used in the composition, as well as methods for making and uses of the composition and virus.

The virus used in the composition according to the present invention is advantageously a poxvirus, particularly a vaccinia virus or an avipox virus, such as fowlpox virus or canarypox virus and more advantageously, ALVAC. The modified recombinant virus can include, e.g., within a non-essential region of the virus genome, a heterologous DNA sequence which encodes an antigenic protein, e.g., derived from PCV2 ORFs, e.g., PCV2 ORF 1 and/or 2.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, e.g., within a non-essential region of the virus genome, a heterologous DNA sequence which encodes an antigenic protein (e.g., derived from PCV2 ORFs, especially ORFS 1 and/or 2) wherein the composition, when administered to a host, is capable of inducing an immunological response specific to the antigen.

In a still further aspect, the present invention relates to a modified recombinant virus having nonessential virus-encoded genetic functions inactivated therein so that the virus has attenuated virulence, and wherein the modified recombinant virus further contains DNA from a heterologous source, e.g., in a nonessential region of the virus genome. The DNA can code for PCV2 genes such as any or all of PCV2 ORF1, ORF2, ORF3, or ORF4 (Meehan et al., 1998), or epitope(s) of interest therefrom. The genetic functions can be inactivated by deleting an open reading frame encoding a virulence factor or by utilizing naturally host-restricted viruses. The virus used according to the present invention is advantageously a poxvirus, e.g., a vaccinia virus or an avipox virus, such as fowlpox virus or canarypox virus.

Advantageously, the open reading frame that is deleted from the poxvirus or virus geneome is selected from the group consisting of J2R, B13R+B14R, A26L, A56R, C7L–K1L, and I4L (by the terminology reported in Goebel et al., 1990); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof.

A suitable modified Copenhagen strain of vaccinia virus is identified as NYVAC (Tartaglia et al., 1992), or a vaccinia virus from which has been deleted J2R, B13R+B14R, A26L, A56R, C7L–K11 and 14L or a thymidine kinase gene, a hemorrhagic region, an A type inclusion body region, a hemagglutinin gene, a host range region, and a large subunit, ribonucleotide reductase (See also U.S. Pat. Nos. 5,364,773, 5,494,807, and 5,762,938, with respect to NYVAC and vectors having additional deletions or inactivations from those of NYVAC that are also useful in the practice of this invention).

Preferably, the poxvirus vector is an ALVAC or, a canarypox virus which was attenuated, for instance, through more than 200 serial passages on chick embryo fibroblasts (Rentschler vaccine strain), a master seed therefrom was subjected to four successive plague purifications under agar from which a plague clone was amplified through five additional passages. (See also U.S. Pat. Nos. 5,756,103 and 5,766,599 with respect to ALVAC and TROVAC (an attenuated fowlpox virus useful in the practice of this invention); and U.S. Pat. Nos. 6,004,777, 5,990,091, 5,770,212, 6,033,904, 5,869,312, 5,382,425, and WO 95/30018, with respect to vectors that also can be used in the practice of this invention, such as vectors having enhanced expression, vectors having functions deleted therefrom and vectors useful with respect to porcine hosts (for instance, vectors useful with porcine hosts can include a poxvirus, including a vaccinia virus, an avipox virus, a canarypox virus, and a swinepox virus), as well as with respect to terms used and teachings herein such as "immunogenic composition", "immunological composition", "vaccine", and "epitope of interest", and dosages, routes of administration, formulations, adjuvants, and uses for recombinant viruses and expression products therefrom).

The invention in yet a further aspect relates to the product of expression of the inventive recombinant poxvirus and uses therefor, such as to form antigenic, immunological or vaccine compositions for treatment, prevention, diagnosis or testing; and, to DNA from the recombinant poxvirus which is useful in constructing DNA probes and PCR primers.

These and other embodiments are disclosed or are obvious from and encompassed by the following detailed description.

BRIEF DESCRIPTION OF THE DRAWINGS

A better understanding of the present invention will be had by referring to the accompanying drawings, incorporated herein by reference, in which:

FIG. 1 (SEQ ID NOS:1 and 2) shows the nucleotide sequence of a 3.7 kilobase pair fragment of ALVAC DNA containing the C6 open reading frame.

FIG. 3 (SEQ ID NOS:8 9 and 10) shows the nucleotide sequence of the 2.5 kilobase pair fragment from pJP 102 donor plasmid from the KpnI (position 653) to the SacI (position 3166) restriction sites.

FIG. 6 (SEQ ID NOs: 14 and 15) shows the nucleotide sequence of the 3.6 kilobase pair fragment from pJP107 donor plasmid from the KpnI (position 653) to the SacI (position 4255) restriction sites.

DETAILED DESCRIPTION

Figure 2:
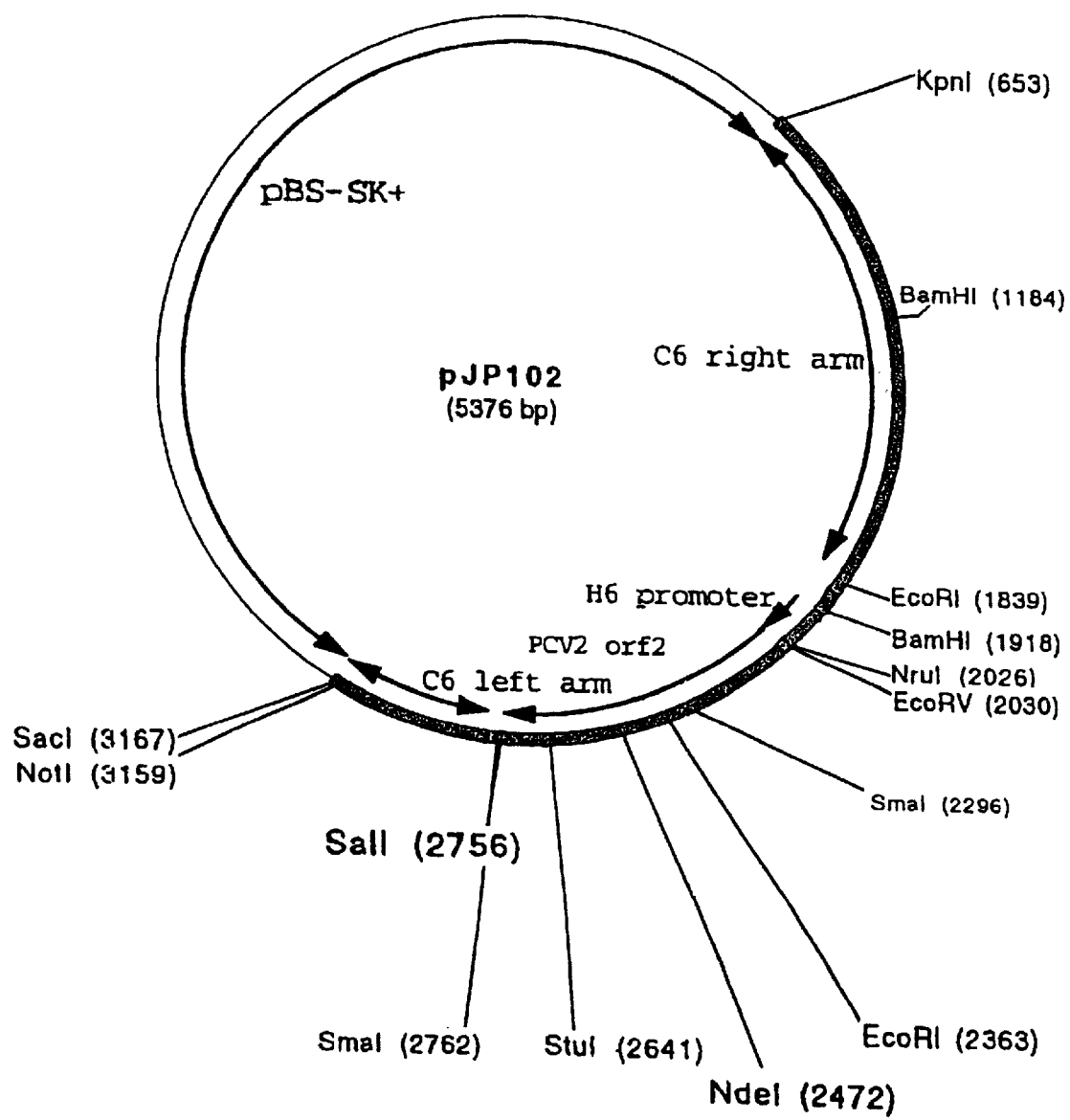
FIG. 2 shows the map of pJP102 donor plasmid.

In one aspect, the present invention relates to a recombinant virus, such as a recombinant poxvirus, containing therein a DNA sequence from PCV2, e.g., in a non-essential region of the poxvirus genome. The poxvirus is advantageously an avipox virus, such as fowlpox virus, especially an attenuated fowlpox virus, or a canarypox virus, especially an attenuated canarypox virus, such as ALVAC.

According to the present invention, the recombinant poxvirus expresses gene products of the foreign PCV2 gene. Specific ORFs of PCV2 are inserted into the poxvirus vector, and the resulting recombinant poxvirus is used to infect an animal. Expression in the animal of PCV2 gene products results in an immune response in the animal to PCV2. Thus, the recombinant poxvirus of the present invention may be used in an immunological composition or vaccine to provide a means to induce an immune response which may, but need not be, protective.

The administration procedure for recombinant poxvirus-PCV2 or expression product thereof, compositions of the invention such as immunological, antigenic or vaccine compositions or therapeutic compositions, can be via a parenteral route (intradermal, intramuscular or subcutaneous). Such an administration enables a systemic immune response, or humoral or cell-mediated responses.

More generally, the inventive poxvirus-PCV2 recombinants, antigenic, immunological or vaccine poxvirus-PCV2 compositions or therapeutic compositions can be prepared in accordance with standard techniques well known to those skilled in the pharmaceutical or veterinary art. Such compositions can be administered in dosages and by techniques well known to those skilled in the medical or veterinary arts taking into consideration such factors as the age, sex, weight, species and condition of the particular patient, and the route of administration. The compositions can be administered alone, or can be co-administered or sequentially administered with compositions, e.g., with "other" immunological, antigenic or vaccine or therapeutic compositions thereby providing multivalent or "cocktail" or combination compositions of the invention and methods employing them. Again, the ingredients and manner (sequential or co-administration) of administration, as well as dosages can be determined taking into consideration such factors as the age, sex, weight, species and condition of the particular patient, and, the route of administration. In this regard, reference is made to U.S. Pat. No. 5,843,456, incorporated herein by reference, and directed to rabies compositions and combination compositions and uses thereof.

Examples of compositions of the invention include liquid preparations for orifice, e.g., oral, nasal, anal, vaginal, peroral, intragastric, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus or antigens may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the Examples below.

The compositions can contain at least one adjuvant compound chosen from the polymers of acrylic or methacrylic acid and the copolymers of maleic anhydride and alkenyl derivative.

The preferred adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among then, there may be mentioned Carbopol® 974P, 934P and 971P.

Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., Nature, 186: 778–780, 4 June 1960, incorporated herein by reference.

From the point of view of their structure, the polymers of acrylic or methacrylic acid and the copolymers EMA® are preferably formed of basic units of the following formula:

$$----\underset{\underset{COOH}{|}}{\overset{\overset{R_1}{|}}{C}}----(CH_2)_{\overline{x}}----\underset{\underset{COOH}{|}}{\overset{\overset{R_2}{|}}{C}}----(CH_2)_{\overline{y}}----$$

in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution which will be neutralized, preferably to physiological pH, in order to give the adjuvant solution into which the vaccine itself will be incorporated. The carboxyl groups of the polymer are then partly in COO⁻ form.

Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCL 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form.

The polymer concentration in the final vaccine composition will be 0.01% to 2% w/v, more particularly 0.06 to 1% w/v, preferably 0.1 to 0.6% w/v. The immunological compositions according to the invention may be associated to at least one live attenuated, inactivated, or sub-unit vaccine, or recombinant vaccine (e.g. poxvirus as vector or DNA plasmid) expressing at least one immunogen from another pig pathogen.

The invention encompasses vectors encoding and expressing equivalent nucleotide sequences, that is to say the sequences which change neither the functionality or the strain specificity (say strain of type 1 and strain of type 2) of the gene considered or those of the polypeptides encoded by this gene. The sequences differing through the degeneracy of the code are, of course, included.

The PCV-2 sequences used in the examples are derived from Meehan et al. (Strain Imp.1010; ORF1 nucleotides 398–1342; ORF2 nucleotides 1381–314; and correspond respectively to ORF4 and ORF13 in U.S. application Ser. No. 09/161,092 of Sep. 25 1998 and to COL4 and COL13 in WO-A-9918214). Other PCV-2 strains and their sequences have been published in WO-A-9918214 and are called Imp1008, Imp999, Imp1011-48285 and Imp1011-48121, as well as in A.L. Hamel et al. J. Virol. June 1998, vol 72, 6: 5262–5267 (GenBank AF027217) and in I. Morozov et al. J. Clinical Microb. September 1998 vol. 36, 9: 2535–2541, as well as GenBank AF086834, AF086835 and AF086836, and give access to equivalent ORF sequences. These sequences, or ORFs therefrom, or regions thereof encoding an antigen or epitope of interest can also be used in the practice of this invention.

The invention also encompasses the equivalent sequences to those used herein and in documents cited herein; for instance, sequences that are capable of hybridizing to the nucleotide sequence under high stringency conditions (see, e.g., Sambrook et al. (1989). Among the equivalent sequences, there may also be mentioned the gene fragments conserving the immunogenicity of the complete sequence, e.g., an epitope of interest.

The homology of the whole genome between PCV types 1 and 2 is about 75%. For ORF1, it is about 86%, and for ORF2, about 66%. On the contrary, homologies between genomes and between ORFs within type 2 are generally above 95%.

Also, equivalent sequences useful in the practice of this present invention, for ORF1, are those sequences having an homology equal or greater than 88%, advantageously 90% or greater, preferably 92% or 95% or greater with ORF1 of strain Imp1010, and for ORF2, are those sequences having an homology equal or greater than 80%, advantageously 85% or greater, preferably 90% or 95% or greater with ORF2 of strain Imp1010.

ORF1 and ORF2 according to Meehan 1998 has the potential to encode proteins with predicted molecular weights of 37.7 kD and 27.8 kD respectively. ORF3 and ORF4 (according to Meehan et al. 1998, correspond to ORF7 and ORF10 respectively in WO-A-9918214) has the potential to encode proteins with predicted molecular weights of 11.9 and 6.5 kD respectively. The sequence of these ORFs is also available in Genbank AF 055392. They can also be incorporated in plasmids and be used in accordance with the invention alone or in combination, e.g. with ORF1 and/or ORF2.

The other ORFs 1–3 and 5, 6, 8–9, 11–12 disclosed in U.S. application Ser. No. 09/161,092 of Sep. 25 1998 (COLs 1–3 and 5, 6, 8–9, 11–12 in WO-A-9918214), or region(s) thereof encoding an antigen or epitope of interest, may be used in the practice of this invention, e.g., alone or in combination or otherwise with each other or with the ORFs 1 and 2 or region(s) thereof encoding antigen(s) or epitope (s).

This invention also encompasses the use of equivalent sequences; for instance, from ORFs of various PCV-2 strains cited herein. For homology, one can determine that there are equivalent sequences which come from a PCV strain having an ORF2 and/or an ORF1 which have an homology as defined above with the corresponding ORF of strain 1010.

For ORF3 according to Meehan, an equivalent sequence has homology thereto that is advantageously, for instance, equal or greater than 80%, for example 85% or greater, preferably 90% or 95% or greater with ORF3 of strain ImplO10. For ORF4 according to Meehan 1998, advantageously an equivalent sequence has homology that is equal or greater than 86%, advantageously 90% or greater, preferably than 95% or greater with ORF4 of strain Imp1010.

From the genomic nucleotide sequence, e.g. those disclosed in WO-A-99 18214, it is routine art to determine the ORFs using a standard software, such as MacVector®. Also, alignment of genomes with that of strain 1010 and comparison with strain 1010 ORFs allows the one skilled in the art to readily determine the ORFs of the genome of another strain (e.g. other strains disclosed in WO-A-99 18214 or in other herein cited documents).

Using software or making sequence alignment is not undue experimentation and provides direct access to equivalent ORFs or nucleic acid molecules.

Nucleotide sequence homology can be determined using the "Align" program of Myers and Miller, ("Optimal Alignments in Linear Space", CABIOS 4, 11–17, 1988, incorporated herein by reference) and available at NCBI. Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})^* 100N_{ref}$, wherein $N_{dif}$ is the total number of non-identical residues in the two sequences when aligned and wherein $N_{ref}$ is the number of residues in one of the sequences. Hence, the DNA sequence AGT-CAGTC will have a sequence similarity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™Suite, Intelligenetics Inc. CA).. When RNA sequences are said to be similar, or have a degree of sequence identity or homology with DNA sequences, thymidine (T) in the DNA sequence is considered equal to uracil (U) in the RNA sequence.

RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25, 3389–3402, incorporated herein by reference) and available at NCBI. The following references (each incorporated herein by reference) provide algorithms for comparing the relative identity or homology of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," *J. Mol. Biol.* 48:444–453 (1970); Smith T F and Waterman M S, "Comparison of Bio-sequences," *Advances in Applied Mathematics* 2:482–489 (1981); Smith T F, Waterman M S and Sadler J R, "Statistical characterization of nucleic acid sequence functional domains," *Nucleic Acids Res.*, 11:2205–2220 (1983); Feng D F and Dolittle R F, "Progressive sequence alignment as a prerequisite to correct phylogenetic trees," *J. of Molec. Evol.*, 25:351–360 (1987); Higgins D G and Sharp P M, "Fast and sensitive multiple sequence alignment on a microcomputer," *CABIOS*, 5: 151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.*, 22:4673–480 (1994); and, Devereux J, Haeberlie P and Smithies O, "A comprehensive set of sequence analysis program for the VAX," *Nucl. Acids Res.*, 12: 387–395 (1984).

This invention not only allows for administration to adult pigs, but also to the young and to gestating females; in the latter case, this makes it possible, in particular, to confer passive immunity onto the newborns (maternal antibodies). Preferably, female pigs are inoculated prior to breeding; and/or prior to serving, and/or during gestation. Advantageously, at least one inoculation is done before serving and it is preferably followed by an inoculation to be performed during gestation, e.g., at about mid-gestation (at about 6–8 weeks of gestation) and/or at the end of gestation (at about 11–13 weeks of gestation). Thus, an advantageous regimen is an inoculation before mating and/o serving and a booster inoculation during gestation. Thereafter, there can be reinoculation before each serving and/or during gestation at about mid-gestation and/or at the end of gestation. Preferably, reinoculations are during gestation. Male pigs also can be inoculated, e.g., prior to mating.

Piglets, such as piglets from vaccinated females (e.g., inoculated as herein discussed), are inoculated within the first weeks of life, e.g., inoculation at one and/or two and/or three and/or four and/or five weeks of life. Preferably, piglets are first inoculated within the first week of life or within the third week of life (e.g., at the time of weaning). Advantageously, such piglets are then boosted two to four weeks later.

The present invention is additionally described by the following illustrative, non-limiting Examples.

EXAMPLES

The invention in a preferred embodiment is directed to recombinant poxviruses containing therein a DNA sequence from PCV2 in a nonessential region of the poxvirus genome. The recombinant poxviruses express gene products of the foreign PCV2 gene. In particular, ORF2 and ORF1 genes encoding PCV2 proteins were isolated, characterized and inserted into ALVAC (canarypox vector) recombinants. The molecular biology techniques used are the ones described by Sambrook et al. (1989).

Cell Lines and Virus Strains. The strain of PCV2 designated Imp.1010-Stoon has been previously described (Meehan et al., 1998). It was isolated from mesenteric lymph node tissues from a diseased pig originating from Canada. Cloning of the PCV2 genome was described by Meehan et al. (1998). Plasmid pGem7Z-Imp1010-Stoon-EcoRI No. 14 contains the PCV2 genome as an EcoRI fragment inserted into the EcoRI site of plasmid pGem-7Z (Promega, Madison, Wis.). The complete nucleotide sequence of the Imp.1010-Stoon PCV2 strain has been determined by Meehan et al. (1998) and is available under the GenBank accession number AF055392.

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC. ALVAC was deposited Nov. 14, 1996 under the terms of the Budapest Treaty at the American Type Culture Collection, ATCC accession number VR-2547.

The generation of poxvirus recombinants involves different steps: (1) construction of an insertion plasmid containing sequences ("arms") flanking the insertion locus within the poxvirus genome, and multiple cloning site (MCS) localized between the two flanking arms (e.g., see Example 1); (2) construction of donor plasmids consisting of an insertion plasmid into the MCS of which a foreign gene expression cassette has been inserted (e.g. see Examples 2 to 5); (3) in vitro recombination in cell culture between the arms of the donor plasmid and the genome of the parental poxvirus allowing the insertion of the foreign gene expression cassette into the appropriate locus of the poxvirus genome, and plaque purification of the recombinant virus (e.g. see Example 6).

PCV2 recombinant immunogens may be used in association with PCV1 immunogens, for immunization of animals against PMWS. In a least preferred approach, PCV1 immunogens may be used without PCV2 immunogens.

Example 1
Construction of Canarypox Insertion Plasmid at C6 Locus

FIG. 1 (SEQ ID NO:1) is the sequence of a 3.7 kb segment of canarypox DNA. Analysis of the sequence revealed an ORF designated C6L initiated at position 377 and terminated at position 2254. The following describes a C6 insertion plasmid constructed by deleting the C6 ORF and replacing it with a multiple cloning site (MCS) flanked by transcriptional and translational termination signals. A 380 bp PCR fragment was amplified from genomic canarypox DNA using oligonucleotide primers C6A1 (SEQ ID NO:2) and C6B1 (SEQ ID NO:3). A 1155 bp PCR fragment was amplified from genomic canarypox DNA using oligonucleotide primers C6C1 (SEQ ID NO:4) and C6D1 (SEQ ID NO:5). The 380 bp and 1155 bp fragments were fused together by adding them together as template and amplifying a 1613 bp PCR fragment using oligonucleotide primers C6A1 (SEQ ID NO:2) and C6D1 (SEQ ID NO:5). This fragment was digested with SacI and KpnI, and ligated into pBluescript SK+ (Stratagene, La Jolla, Calif., USA) digested with SacI/KpnI. The resulting plasmid, pC6L was confirmed by DNA sequence analysis. It consists of 370 bp of canarypox DNA upstream of C6 ("C6 left arm"), vaccinia early termination signal, translation stop codons in six reading frames, an MCS containing SmaI, PstI, XhoI and EcoRI sites, vaccinia early termination signal, translation stop codons in six reading frames and 1156 bp of downstream canary pox sequence ("C6 right arm").

Plasmid pJP099 was derived from pC6L by ligating a cassette containing the vaccinia H6 promoter (described in Taylor et al. (1988c), Guo et al. (1989), and Perkus et al. (1989)) coupled to a foreign gene into the SmaI/EcoRI sites of pC6L. This plasmid pJP099 contains a unique EcoRV site and a unique NruI site located at the 3' end of the H6 promoter, and a unique SalI site located between the STOP codon of the foreign gene and the C6 left arm. The ~4.5 kb EcoRV/SalI or NruI/SalI fragment from pJP099 contains therefore the plasmid sequence (pBluescript SK+; Stratagene, La Jolla, Calif., USA), the 2 C6 arms and the 5' end of the H6 promoter until the EcoRV or NruI site.

Sequences of the Primers
Primer C6A1 (SEQ ID NO:3)
ATCATCGAGCTCGCGGCCGCCTATCAAAAGTCTT-AATGAGTT
Primer C6B1 (SEQ ID NO:4)
GAATTCCTCGAGCTGCAGCCCGGGTTTTTATAG-CTAATTAGTCATTTTTTCGTAAGTA AGTATTTT-TATTTAA
Primer C6C1 (SEQ ID NO:5)
C C C G G G C T G C A G C T C G A G G A A T T C T T T T-TATTGATTAACTAGTCAAATGAGTATATA TAAT-TGAAAAAGTAA
Primer C6D1 (SEQ ID NO:6)
GATGATGGTACCTTCATAAATACAAGTTTGATTAAA-CTTAAGTTG Example 2
Construction of ALVACC Donor Plasmid for PCV2 ORF2

Plasmid pGem7Z-Imp1010-Stoon-EcoRI No. 14, containing the PCV2 genome as an EcoRI fragment in plasmid pGem-7Z, was digested with EcoRI, and a 1768 bp fragment was isolated and ligated.

In order to insert PCV2 ORF 2 into an appropriate ALVAC insertion vector: Primers JP760 (SEQ ID NO:6) and JP773 (SEQ ID NO:7) were used to amplify PCV2 ORF 2 from the 1768 bp ligated EcoRI fragment (see above) resulting in PCR J1304. Primer JP760 (SEQ ID NO:7) contains the 3' end of the H6 promoter from EcoRV and the 5' end of PCV2 ORF 2. Primer JP773 (SEQ ID NO:8) contains the 3' end of PCV2 ORF 2 followed by a SalI site. The product of PCR J1304 was then digested with EcoRV/SalI and cloned as a ~750 bp fragment into a ~4.5 kb EcoRVlSalI fragment from pJP099 (see above in Example 1). The resulting plasmid was confirmed by sequence analysis and designated pJP102 (see the map of pJP102 in FIG. 2 and the sequence (SEQ ID NO:9) in FIG. 3). The sequence of ORF 2 matches sequence available in GenBank, Accession Number AF055392. The donor plasmid pJP102 (linearized with NotI) was used in an in vitro recombination (IVR) test to generate ALVAC recombinant vCP1614 (see Example 6).
Sequence of the Primers
JP760 (SEQ ID NO:7)
CAT-CAT-CAT-GAT-ATC-CGT-TAA-GTT-TGT-ATC-GTA-ATG-ACG-TAT-CCA-AGG-AGG-CG
JP773 (SEQ ID NO:8)
TAC-TAC-TAC-GTC-GAC-TTA-GGG-TTT-AAG-TGG-GGG-GTC Example 3
Construction of an ALVACC Donor Plasmid for PCV2 ORF2 and ORF1

Figure 4:
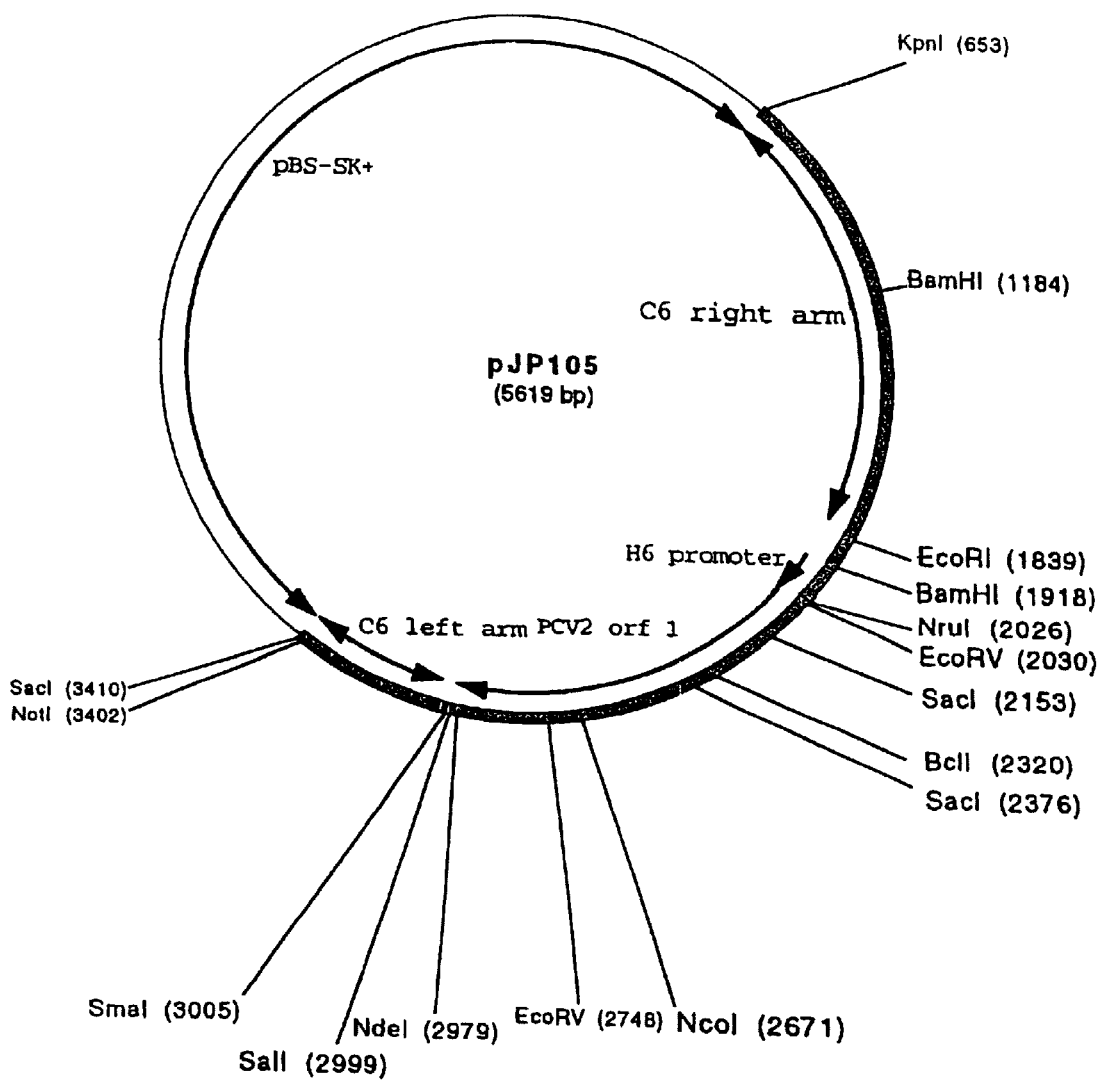
FIG. 4 shows the map of pJP105 donor plasmid.

PCV2 ORF1 was amplified by PCR using primers JP774 (SEQ ID NO:9) and JP775 (SEQ ID NO:10) on plasmid pGem7Z-Imp1010-Stoon-EcoRI No. 14 resulting in PCR J1311. Primer JP774 (SEQ ID NO:10) contains the 3' end of the H6 promoter from NruI and the 5' end of PCV2 ORF1. Primer JP775 (SEQ ID NO:11) contains the 3' end of PCV2 ORF1 followed by a SalI site. The product of PCR J1311 (~1 Kb) was cloned into pCR2.1 (Invitrogen, Carlsbad, Calif.). The resulting plasmid was confirmed by sequence analysis and designated pJP104. The sequence of ORF1 matches sequence available in GenBank, Accession Number AF055392. A ~970 bp NruII/SalI fragment was isolated from pJP104 and cloned into a ~4.5 kb NruI/SalI fragment from pJP099 (see Example 1), resulting in a plasmid which was confirmed by restriction analysis and designated pJP105 (see FIG. 4). The donor plasmid pJP105 could be used in an in vitro recombination test (described in Example 6) to generate ALVAC recombinant expressing the PCV2 ORF1.

Figure 5:
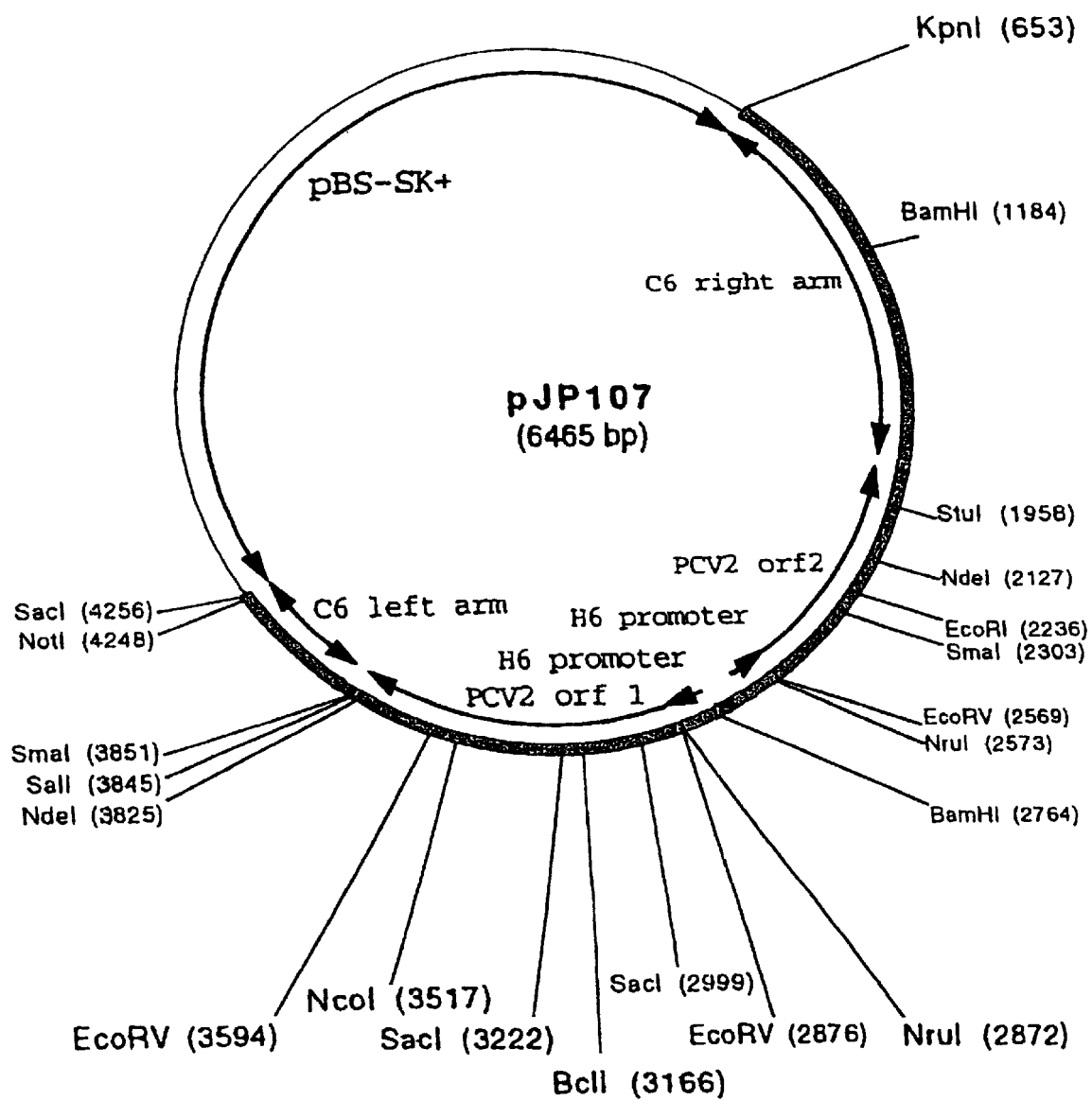
FIG. 5 shows the map of pJP107 donor plasmid.

A ~838 bp BamHI/SalI from pJP102 (see Example 2) was blunted using the Klenow fragment of DNA polymerase, and was cloned into the Klenow-blunted EcoRI site of pJP105. Clones were checked for orientation of insert by restriction analysis and a head-to-head orientation was chosen. This plasmid was confirmed by sequence analysis and designated pJP107 (see the map of pJP107 in FIG. 5 and the sequence (SEQ ID NO:11) in FIG. 6). The donor plasmid pJP107 (linearized with NotI) was used in an in vitro recombination 5 (IVR) test to generate the ALVAC recombinant vCP1615 (see Example 6).

Sequence of the Primers
JP774 (SEQ ID NO:7)
CAT-CAT-CAT-TCG-CGA-TAT-CCG-TTA-AGT-TTG-TAT-CGT-AAT-GCC-CAG-CAA-GAA-GAA-TGG
JP775 (SEQ ID NO:12)
TAC-TAC-TAC-GTC-GAC-TCA-GTA-ATT-TAT-TTC-ATA-TGG Example 4
Construction of ALVACC Donor Plasmid for PCV1 RF2

Plasmid pPCV1 (B. Meehan et al. J. Gen. Virol. 1997. 78. 221–227), containing the PCV1 genome as a PstI fragment in plasmid pGem-7Z, was used as a template to amplify the PCV1 ORF2.

In order to insert PCV2 ORF 2 into an appropriate ALVAC insertion vector: Primers JP787 (SEQ ID NO:16) and JP788 (SEQ ID NO:17) were used to amplify PCV1 ORF 2 from plasmid pPCV1 (see above) resulting in PCR J1315. Primer JP787 (SEQ ID NO:16) contains the 3' end of the H6 promoter from EcoRV and ORF 2 followed by a SalI site. The product of PCR J1315 was then digested with EcoRV/SalI and cloned as a ~750 bp fragment into a ~4.5 kb EcoRV/SalI fragment from pJP099 (see above in Example 1). The resulting plasmid was confirmed by sequence analysis and designated pJP113. The sequence of ORF 2 matches sequence available in GenBank, Accession Number U49186. The donor plasmid pJP113 (linearized with NotI) was used in an in vitro recombination (IVR) test to generate ALVAC recombinant vCP1621 (see Example 7).

Sequence of the Primers

JP787 (SEQ ID NO:17)

CAT-CAT-CAT-GAT-ATC-CGT-TAA-GTT-TGT-ATC-GTA-ATG-ACG-TGG-CCA-AGG-AGG-CG

JP788 (SEQ ID NO:13)

TAC-TAC-TAC-GTC-GAC-TTA-TTT-ATT-TAG-AGG-GTC-TTT-TAG-G

Example 5

Construction of an ALVACC Donor Plasmid for PCV1 RF2 and ORF1

Plasmid pPCV1 (see Example 4 above), containing the PCV1 genome as a PstI fragment in plasmid pGem-7Z, was digested with PstI, and a 1759 bp fragment was isolated and ligated.

Primers JP789 (SEQ ID NO:14) and JP790 (SEQ ID NO:15) were used to amplify PCV1 ORF1 from the 1759 bp ligated PstI fragment (see above), resulting in PCR J1316. Primer JP789 (SEQ ID NO:14) contains the 3' end of the H6 promoter from NruI and the 5' end of PCV1 ORF1. Primer JP790 (SEQ ID NO:15) contains the 3' end of PCV1 ORF1 followed by a SalI site. The product of PCR J1316 (~1 Kb) was cloned into pCR2.1 (Invitrogen, Carlsbad, Calif.). The resulting plasmid was confirmed by sequence analysis and designated pJP114. The sequence of ORF1 matches sequence available in GenBank, Accession Number U49186. A ~970 bp NruI/SalI fragment was isolated from pJP114 and cloned into a ~4.5 kb NruI/SalI fragment from pJP099 (see Example 1), resulting in a plasmid which was confirmed by restriction analysis and designated pJP115. The donor plasmid pJP115 could be used in an in vitro recombination test (described in Example 7) to generate ALVAC recombinant expressing the PCV1 ORF1.

A ~838 bp BamHI/SalI from pJP113 (see Example 4) was blunted using the Klenow fragment of DNA polymerase, and was cloned into the Klenow-blunted EcoRI site of pJP115. Clones were checked for orientation of insert by restriction analysis and a head-to-head orientation was chosen. This plasmid was confirmed by sequence analysis and designated pJP117. The donor plasmid pJP117 (linearized with NotI) was used in an in vitro recombination (IVR) test to generate the ALVAC recombinant vCP1622 (see Example 7).

Sequence of the Primers

JP789 (SEQ ID NO:18)

CAT-CAT-CAT-TCG-CGA-TAT-CCG-TTA-AGT-TTG-TAT-CGT-AAT-GCC-AAG-CAA-GAA-AAG-CGG

JP790 (SEQ ID NO:19)

TAC-TAC-TAC-GTC-GAC-TCA-GTA-ATT-TAT-TTT-ATA-TGG

Example 6

Generation of ALVAC-PCV2 RECOMBINANTS

Plasmids pJP102 (see Example 2 and FIG. 2) and pJP107 (see Example 3 and FIG. 5) were linearized with NotI and transfected into ALVAC infected primary CEF cells by using the calcium phosphate precipitation method previously described (Panicali and Paoletti, 1982; Piccini et al., 1987). Positive plaques were selected on the basis of hybridization to specific PCV2 radiolabeled probes and subjected to four sequential rounds of plaque purification until a pure population was achieved. One representative plaque from each IVR was then amplified and the resulting ALVAC recombinants were designated vCP1614 and vCP1615. The vCP1614 virus is the result of recombination events between ALVAC and the donor plasmid pJP102, and it contains the PCV2 ORF2 inserted into the ALVAC C6 locus. The vCP1615 virus is the result of recombination events between ALVAC and the donor plasmid pJP107, and it contains the PCV2 ORF2 and ORF1 inserted into the ALVAC C6 locus in a head-to-head orientation.

In a similar fashion, a recombinant ALVAC expressing only PCV2 ORF1 can be generated using the donor plasmid pJP105 described in Example 3.

Immunofluorescence. In order to determine if the PCV2 proteins were expressed in ALVAC recombinant infected Vero cells, immunofluorescence (IF) analysis was performed. Infected Vero cells were washed with PBS 24 hrs after infection (m.o.i. of approx. 10) and fixed with 95% cold aceton for 3 minutes at room temperature. Five monoclonal antibody (MAb) preparations (hybridoma supernatant) specific for PCV2 ORF1 (PCV2 199 1D3GA & PCV2 210 7G5GD) or ORF2 (PCV2 190 4C7CF, PCV2 190 2B1BC & PCV2 190 3A8BC) were used as the first antibody. These specific monoclonal antibodies were obtained from Merial-Lyon. Monoclonal antibodies can also be obtained following the teachings of documents cited herein, e.g. WO-A-99 18214, 1998, French applications Nos. 97/12382, 98/00873, 98/03707, filed Oct. 3, 1997, Jan. 22, 1998, and Mar. 20, 1998, and WO99/29717, incorporated herein by reference. The IF reaction was performed as described by Taylor et al. (1990).

PCV2 specific immunofluorescence with the three ORF2-specific antibodies could be detected in cells infected with vCP1614 and cells infected with vCP1615. PCV2 specific immunofluorescence with the two ORF1-specific antibodies could be detected in cells infected with vCP1615 only. These results indicated that, as expected, vCP1614 expresses only ORF2, whereas vCP1615 expresses both ORF1 and ORF2. No fluorescence was detected in parental ALVAC infected Vero cells, nor in uninfected Vero cells.

Example 7
Generation of ALVAC-PCV1 Recombinants

Plasmids pJP113 (see Example 4) and pJP117 (see Example 5) were linearized with NotI and transfected into ALVAC infected primary CEF cells by using the calcium phosphate precipitation method previously described (Panicali and Paoletti, 1982; Piccini et al., 1987). Positive plaques were selected on the basis of hybridization to specific PCV1 radiolabeled probes and subjected to four sequential rounds of plaque purification until a pure population was achieved. One representative plaque from each IVR was then amplified and the resulting ALVAC recombinants were designated vCP1621 and vCP1622. The vCP1621 virus is the result of recombination events between ALVAC and the donor plasmid pJP113, and it contains the PCV1 ORF2 inserted into the ALVAC C6 locus. The vCP1622 virus is the result of recombination events between ALVAC and the donor plasmid pJP117, and it contains the PCV1 ORF2 and ORF1 inserted into the ALVAC C6 locus in a head-to-head orientation.

In a similar fashion, a recombinant ALVAC expressing only PCV1 ORF1 can be generated using the donor plasmid pJP115 described in Example 5.

Immunofluorescence. In order to determine if the PCV1 proteins were expressed in ALVAC recombinant infected Vero cells, immunofluorescence (IF) analysis was performed. Infected Vero cells were washed with PBS 24 hrs after infection (m.o.i. of approx. 10) and fixed with 95% cold aceton efor 3 minutes at room temperature. A specific anti-PCV1 pig polyclonal serum (Allan G. et al. Vet. Microbiol. 1999. 66: 115–123) was used as the first antibody. The IF reaction was performed as described by Taylor et al. (1990).

PCV1 specific immunofluorescence could be detected in cells infected with vCP1621 and cells infected with vCP1622. These results indicated that, as expected, vCP1621 and vCP1622 express PCV1-specific products. No fluorescence was detected with a PCV2-specific pig polyclonal serum in cells infected with vCP1621 and in cells infected with vCP1622. No fluorescence was detected in parental ALVAC infected Vero cells, nor in uninfected Vero cells.

Example 8
Formulation of Recombinant Canarypox Viruses with Carbopol™ 974P

For the preparation of vaccines, recombinant canarypox viruses vCP1614 and vCP1615 (Example 6) can be mixed with solutions of carbomer. In the same fashion, recombinant canarypox viruses vCP1621 and vCP1622 (Example 7) can be mixed with solutions of carbomer. The carbomer component used for vaccination of pigs according to the present invention is the Carbopol™ 974P manufactured by the company BF Goodrich (molecular weight of # 3,000, 000). A 1.5 % Carbopol™ 974P stock solution is first prepared in distilled water containing 1 g/l of sodium chloride. This stock solution is then used for manufacturing a 4 mg/ml Carbopol™ 974P solution in physiological water. The stock solution is mixed with the required volume of physiological water, either in one step or in several successive steps, adjusting the pH value at each step with a 1N (or more concentrated) sodium hydroxide solution to get a final pH value of 7.3–7.4. This final Carbopol™ 974P solution is a ready-to-use solution for reconstituting a lyophilized recombinant virus or for diluting a concentrated recombinant virus stock. For example, to get a final viral suspension containing $10^e8$ pfu per dose of 2 ml, one can dilute 0,1 ml of a $10^e9$ pfU/ml stock solution into 1,9 ml of the above Carbopol™ 974P 4 mg/ml ready-to-use solution. In the same fashion, Carbopol™ 974P 2 mg/ml ready-to-use solutions can also be prepared.

Example 9
Immunization of Pigs and Subsequent Challenge
9.1. Immunization of 1 Day-Old Piglets Groups of piglets, caesarian-derived at Day 0, are placed into isolators. The piglets are vaccinated by intramuscular route at Day 2 with various vaccine solutions. Vaccine viral suspensions are prepared by dilution of recombinant viruses stocks in sterile physiological water (NaCl 0.9 %). Suitable ranges for viral suspensions can be determined empiracally, but will generally range from $10^6$ to $10^{10}$, and preferably about $10^{10}$, pfu/dose. Vaccine solutions can also be prepared by mixing the recombinant virus suspension with a solution of Carbopol™ 974P, as described in Example 8.

Piglets are vaccinated either with:
Recombinant virus vCP1614 (Example 2);
Recombinant virus vCP1615 (Example 3);
Recombinant virus vCP1614 mixed with Carbopol (4 mg/ml solution); or
Recombinant virus vCP1615 mixed with Carbopol (4 mg/ml solution).

The viral suspensions contain $10^8$ plaque forming units (pfu) per dose. Each viral suspension is injected by intramuscular route under a volume of 1 ml. The intramuscular injection is administered into the muscles of the neck.

Two injections of viral suspensions are administered at Day 2 and Day 14 of the experiment. A challenge is done on Day 21 by an oronasal administration of a viral suspension prepared from a culture of PCV-2 virulent strain. After challenge, piglets are monitored during 3 weeks for clinical signs specific of the post-weaning multisystemic syndrome. The following signs are scored:

Rectal temperature: daily monitoring for 2 weeks post-challenge, then 2 measures of rectal temperature during the third week.
Weight: piglets are weighed right before the challenge, and then weekly during the first 3 weeks post-challenge.
Blood samples are taken at Day 2, day 14, Day 21, Day 28, Day 35 and Day 42 of the experiment in order to monitor viremia levels and anti-PCV-2 specific antibody titers.
Necropsies: at Day 42, all surviving piglets are humanely euthanized and necropsied to look for specific PWMS macroscopic lesions. Tissue samples are prepared from liver, lymph nodes, spleen, kidneys and thymus in order to look for specific histological lesions.

9.2. Immunization OF 5–7 Week-Old Piglets

5–7 week-old piglets, free of anti-PCV-2 specific maternal antibodies, are vaccinated by intramuscular route with various vaccine solutions. Vaccine viral suspensions are prepared by dilution of recombinant viruses stocks in sterile physiological water (NaCl 0.9%). Vaccine solutions can also be prepared by mixing the recombinant virus suspension with a solution of Carbopol™ 974P, as described in Example 8.

Piglets are vaccinated either with:
Recombinant virus vCP1614 (Example 2);
Recombinant virus vCP1615 (Example 3);
Recombinant virus vCP1614 mixed with Carbopol (4 mg/ml solution); or
Recombinant virus vCP1615 mixed with Carbopol (4 mg/ml solution).

The viral suspensions contain $10^8$ plaque forming units (pfu) per dose. Each viral suspension is injected by intramuscular route under a volume of 2 ml. The intramuscular injection is administered into the muscles of the neck. Two injections of the viral suspensions are administered at Day 0 and Day 21 of the experiment. A challenge is done at Day 35 by an oronasal administration of a viral suspension prepared from a culture of PCV-2 virulent strain. After challenge, piglets are monitored during 8 weeks for clinical signs specific of the post-weaning multisystemic syndrome. The clinical monitoring is identical to the one described in Example 9.1. except that total duration of monitoring is 8 weeks instead of 3 weeks.

Necropsies are done throughout the experiment for piglets dying from the challenge and at the end of the experiment (Day 97) for all surviving piglets. Tissue samples are the same as described in Example 9.1.

9.3. Immunization of Newborn Piglets

Groups of 3 or 4 piglets, caesarian-delivered day 0 are placed into isolators. Day 2 the piglets are vaccinated with $10^8$ pfu of vCP1614, vCP1615 or parental ALVAC vector in 1 ml of PBS by intramuscular route on the side of the neck. A second injection of vaccine or placebo is administered at day 14. Vaccination with ALVAC recombinant is well tolerated by piglets and no evidence of adverse reaction to vaccination is noted. The piglets are challenged day 21 by oronasal administration of a PCV-2 viral suspension, 1 ml in each nostril. Day 45 necropsies are performed and samples of tissues are collected for virus isolation. Necropsy results: PMWS is characterized generally by lymphadenopathy and more rarely by hepatitis or nephritis. So the gross findings in lymph nodes are scored for each piglet in the following manner: 0=no visible enlargement of lymph nodes; 1=mild lymph nodes enlargement, restricted to bronchial lymph nodes; 2=moderate lymph nodes enlargement, restricted to bronchial lymph nodes; 3=severe lymph nodes enlargement, extended to bronchial, submandibullar prescapular and inguinal lymph nodes.

| Groups | Scores |
|---|---|
| vCP 1614 | 0.5 |
| | 0.0 |
| | 0.0 |
| | 1.0 |
| mean | 0.38 |
| standard deviation | 0.48 |
| vCP 1615 | 0.0 |
| | 0.5 |
| | 0.5 |
| | 1.0 |
| mean | 0.5 |
| standard deviation | 0.41 |
| Controls | 2.0 |
| | 2.5 |
| | 2.5 |
| | 2.5 |
| mean | 2.38 |
| standard deviation | 0.25 |

Bronchial lymphadenopathy for PCV-2 is a prominent gross finding. A significant reduction of the lymph nodes lesion in relation to control group is observed after immunization with vCP 1614 and vCP1615 ($p \leq 0.05$).

Having thus described in detail preferred embodiments of the present invention, it is to be understood that the invention defined by the appended claims is not to be limited to particular details set forth in the above description as many apparent variations thereof are possible without departing from the spirit or scope of the present invention.

REFERENCES

1. Clark, E. G. Proc. Amer. Assoc. Swine Pract., pp. 499–501 (1997).
2. Edbauer, C., R. Weinberg, J. Taylor, A. Rey-Senelonge, J. F. Bouquet, P. Desmettre and E. Paoletti, Virology 179, 901–904 (1990).
3. Ellis, J., L. Hassard, E. Clark, J. Harding, G. Allan, P. Willson, J. Strakappe, K. Martin, F. McNeilly, B. Meehan, D. Todd, D. Haines, Can. Vet. J. 39, 44–51 (1998).
4. Goebel, S. J., G. P. Johnson, M. E. Perkus, S. W. Davis, J. P. Winslow, E. Paoletti, Virology 179, 247–266, 517–563 (1990).
5. Guo, P., S. Goebel, S. Davis, M. E. Perkus, B. Languet, P. Desmettre, G. Allen, and E. Paoletti, J. Virol. 63, 4189–4198 (1989).
6. Hamel, A. L., L. L. Lin and G. P. S. Nayar, J. Virol. 72, 5262–5267 (1998).
7. Harding J. C., Proc. Am. Assoc. Swine Pract. 28, 503 (1997).
8. Mankertz, A., J. Mankertz, K. Wolf, H.-J. Buhk, Gen. Virol. 79, 381–384 (1998a).
9. Mankertz, J., H.-J. Buhk, G. Blaess, A. Mankertz, Virus Gene 16, 267–276 (1998b).
10. Matthews, R. E. F., Intervirology 17, 42–44 (1982).
11. Meehan, B. M., J. L. Creelan, M. S. McNulty, D. Todd, J. Gen. Virol. 78, 221–227 (1997).
12. Meehan, B. M., F. McNeilly, D. Todd, S. Kennedy, V. A. Jewhurst, J. A. Ellis, L. E. Hassard, E. G. Clark, D. M. Haines, G. M. Allan, J. Gen. Virol. 79, 2171–2179 (1998).
13. Nayar, G. P. S., A. Hamel and L. Lin. Can. Vet. J. 38, 385–386 (1997).
14. Panicali, D. and E. Paoletti, Proc. Natl. Acad. Sci. USA 79, 4927–4931 (1982).
15. Paoletti, E., B. R. Lipinskaks, C. Samsonoff, S. Mercer, and D. Panicali, Proc. Natl. Acad. Sci. U.S.A. 81, 193–197 (1984).
16. Perkus, M. E., K. Limbach, and E. Paoletti, J. Virol. 63, 3829–3836 (1989).
17. Piccini, A., M. E. Perkus, and E. Paoletti, In Methods in Enzymology, Vol. 153, eds. Wu, R., and Grossman, L., (Academic Press) pp. 545–563 (1987).
18. Sambrook, J., E. F. Fritsch, and T. Maniatis, In Molecular cloning: A laboratory manual, 2nd edition, (Cold Spring Harbor Press, NY) (1989).
19. Tartaglia, J., J. Winslow, S. Goebel, G. P. Johnson, J. Taylor, and E. Paoletti, J. Gen. Virol. 71, 1517–1524 (1990).
20. Tartaglia, J., Perkus M E, Taylor J, Norton E K, Audonnet J C, Cox W I, Davis S W, van der Hoeven J, Meignier B, Riviere M, and E. Paoletti, Virology 188, 217–32 (1992).
21. Taylor, J., R. Weinberg, B. Languet, P h. Desmettre and E. Paoletti, Vaccine 6, 497–503 (1988a).
22. Taylor, J. and E. Paoletti, Vaccine 6, 466–468 (1988b).
23. Taylor, J., R. Weinberg, Y. Kawaoka, R. Webster and E. Paoletti, Vaccine 6, 504–508 (1988c).

24. Taylor, J., C. Edbauer, A. Rey-Senelonge, J. F. Bouquet, E. Norton, S. Goebel, P. Desmettre and E. Paoletti, J. Virol. 64, 1441–1450 (1990).
25. Taylor, J., C. Trimarchi, R. Weinberg, B. Languet, F. Guillemin, P. Desmettre and E. Paoletti, Vaccine 9, 190–193 (1991).
26. Taylor J, Weinberg R, Tartaglia J, Richardson C, Alkhatib G, Briedis D, Appel M, Norton E, Paoletti E., Virology187, 321–328 (1992).
27. Todd, D., F. D. Niagro, B. W. Ritchie, W. Curran, G. M. Allan, P. D. Lukert, K. S. Latimer, W. L. Steffens, M. S. McNulty, Arch. Virol. 117, 129–135 (1991).

---

What is claimed is:

1. A recombinant poxvirus comprising an isolated DNA molecule selected from the group consisting of ORFs 1 to 13 of porcine circovirus type II, wherein the poxvirus is:
   ALVA C, or
   a poxvirus having all the identifying characteristics of ALVAC.

2. The recombinant poxvirus of claim 1 wherein the recombinant poxvirus is a recombinant ALVAC canarypox virus.

3. The recombinant poxvirus of claim 2 wherein the isolated DNA molecule is in the C6 locus of the ALVAC canarypox virus genome.

4. The recombinant poxvirus of claim 1 wherein the isolated DNA molecule comprises PCV2 ORF1, PCV2 ORF2, or PCV2 ORF1 and PCV2 ORF2.

5. The recombinant poxvirus of claim 4 wherein the isolated DNA molecule is in the C6 locus of the ALVAC canarypox virus genome.

6. An immunological composition comprising the recombinant poxvirus of any one of claims 1 to 3, 4 or 5, and a carrier.

7. The immunological composition of claim 6, which contains an adjuvant.

8. The immunological composition of claim 7, wherein the adjuvant is a carbomer.

9. A method of expressing a porcine circovirus ORF in a cell cultured in vitro comprising introducing into the cell the recombinant poxvirus as claimed in any one of claims 1 to 3, 4 or 5 under conditions which allow expression of the isolated DNA molecule by the recombinant poxvirus.

10. A method for inducing an immunological response against porcine circovirus in a host capable of an immunological response against porcine circovirus comprising administering to the host the recombinant poxvirus of any one of claims 1 to 3, 4 or 5.

11. The method of claim 10 wherein the recombinant poxvirus is administered with an adjuvant.

12. The method of claim 11 wherein the adjuvant is a carbomer.

13. An immunological composition comprising a recombinant avipox virus comprising an isolated DNA molecule selected from the group consisting of ORFs 1 to 13 of porcine circovirus type II, and a carbomer adjuvant.

14. The immunological composition of claim 13 wherein the isolated DNA molecule encodes PCV2 ORF1, PCV2 ORF2, or PCV2 ORF1 and PCV2 ORF2.

15. The immunological composition of any one of claim 13 or 14 wherein the avipox virus is a canarypox virus.

16. A recombinant avipox virus comprising an isolated DNA molecule comprising porcine circovirus type II (PCV2) open reading frames 1 and 2 (ORFs 1 and 2).

17. The recombinant avipox virus of claim 16 which is a recombinant canarypox virus.

18. An immunological composition comprising the recombinant avipox virus of any one of claim 16 or 17 and a carrier.

19. A method of expressing a gene product in a cell cultured in vitro comprising introducing into the cell the recombinant avipox virus as claimed in any one of claim 16 or 17 under conditions which allow expression of the isolated DNA molecule by the recombinant avipox virus.

20. A method for inducing an immunological response against porcine circovirus in a host capable of an immunological response against porcine circovirus comprising administering to the host the recombinant avipox virus of any of claim 16 or 17.

21. A method for inducing an immunological response against porcine circovirus in a host capable of an immunological response against porcine circovirus comprising administering to the host the composition of any one of claim 13 or 14.

22. A method for inducing an immunological response against porcine circovirus in a host capable of an immunological response against porcine circovirus comprising administering to the host the composition of claim 15.

23. The method of claim 10 wherein the host is a porcine.

24. The method of claim 20 wherein the host is a porcine.

25. The method of claim 21 wherein the host is a porcine.

26. The method of claim 22 wherein the host is a porcine.

* * * * *

UNITED STATES PATENT AND TRADEMARK OFFICE
CERTIFICATE OF CORRECTION

PATENT NO. : 6,497,883 B1
DATED : December 24, 2002
INVENTOR(S) : Michel Bublot et al.

It is certified that error appears in the above-identified patent and that said Letters Patent is hereby corrected as shown below:

<u>Title page,</u>
Item [73], Assignee, change "Lyons" to -- Lyon --.

Signed and Sealed this

Fourth Day of March, 2003

JAMES E. ROGAN
*Director of the United States Patent and Trademark Office*